United States Patent
Harada

(10) Patent No.: US 12,185,914 B2
(45) Date of Patent: Jan. 7, 2025

(54) DISTAL END CAP DETACHMENT JIG AND ENDOSCOPE

(71) Applicant: FUJIFILM Corporation, Tokyo (JP)

(72) Inventor: Takashi Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 213 days.

(21) Appl. No.: 17/744,741

(22) Filed: May 16, 2022

(65) Prior Publication Data

US 2022/0369909 A1    Nov. 24, 2022

(30) Foreign Application Priority Data

May 24, 2021    (JP) ................................ 2021-086948

(51) Int. Cl.
*A61B 1/00*    (2006.01)

(52) U.S. Cl.
CPC ...... *A61B 1/00137* (2013.01); *A61B 1/00101* (2013.01); *A61B 1/00128* (2013.01); *A61B 1/0014* (2013.01)

(58) Field of Classification Search
CPC ............ A61B 1/00101; A61B 1/00128; A61B 1/00137; A61B 1/0014
See application file for complete search history.

(56) References Cited

U.S. PATENT DOCUMENTS

| 2003/0088155 | A1* | 5/2003 | Ishibiki | A61B 1/00089 600/127 |
| 2018/0228348 | A1* | 8/2018 | Yamaya | A61B 1/00091 |
| 2022/0061637 | A1* | 3/2022 | Harada | A61B 1/00098 |

FOREIGN PATENT DOCUMENTS

| JP | 3283135 | 5/2002 |
| WO | 2018051626 | 3/2018 |

* cited by examiner

*Primary Examiner* — Aaron B Fairchild
(74) *Attorney, Agent, or Firm* — JCIPRNET

(57) ABSTRACT

Provided are a distal end cap detachment jig and an endoscope capable of simply and easily detaching a distal end cap from a distal end portion body.

A distal end cap detachment jig that is used to detach, from a distal end portion body of an endoscope insertion part, a distal end cap which is attachable to and detachable from the distal end portion body and which is provided with a locking portion for mounting capable of being locked to the distal end portion body when the distal end cap is mounted on the distal end portion body, the distal end cap detachment jig including: a jig body having an accommodation space portion of which one end is provided with an opening portion; a locking release portion provided in the jig body; and a holding portion provided in the jig body, in which in a case where the distal end cap is accommodated in the accommodation space portion, the locking release portion is in a locking release state in which locking of the locking portion with respect to the distal end portion body is released and the holding portion is in a holding state in which the distal end cap is held by the holding portion, to make the distal end cap integral with the jig body so that the distal end cap is capable of being pulled out from the distal end portion body.

13 Claims, 23 Drawing Sheets

FIG. 5
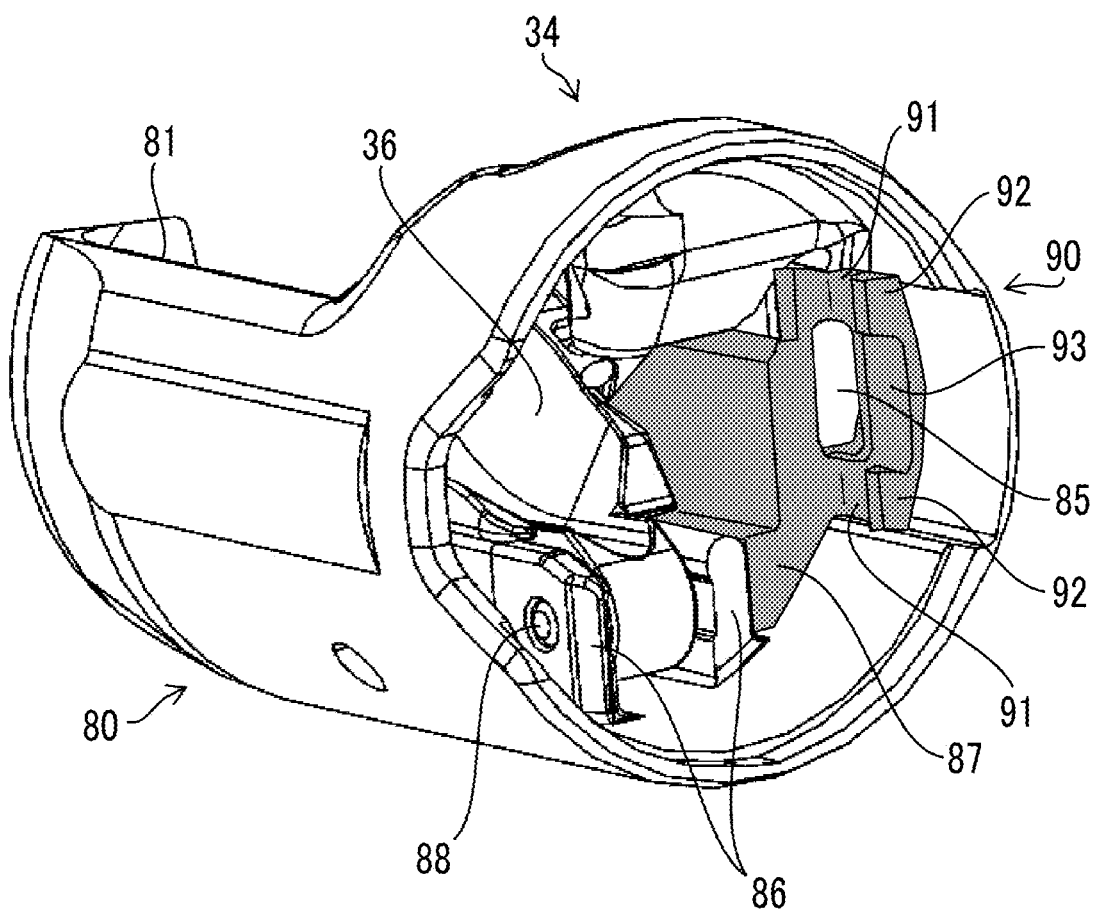
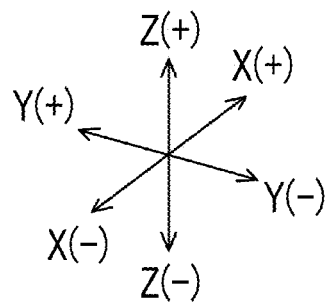

FIG. 9
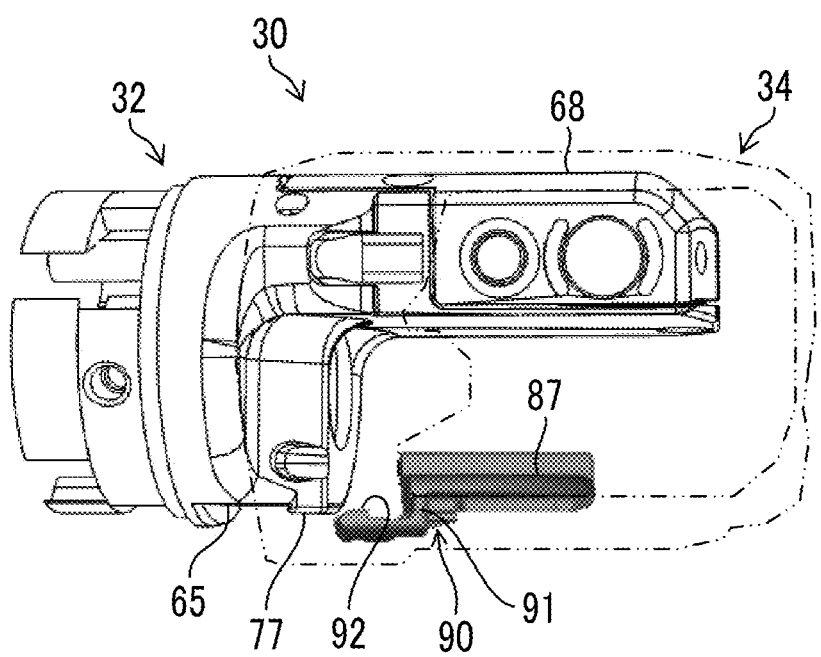
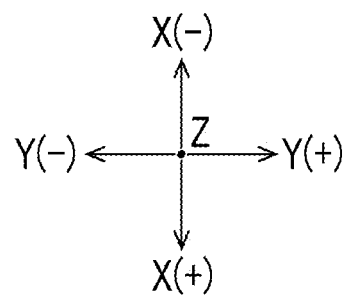

FIG. 21
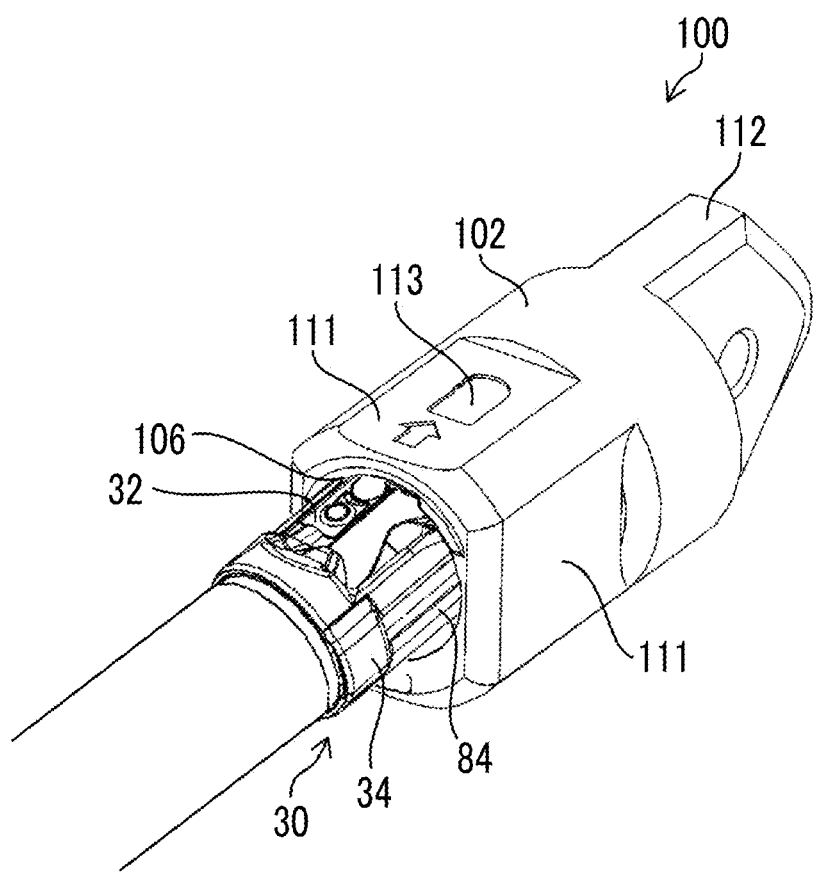
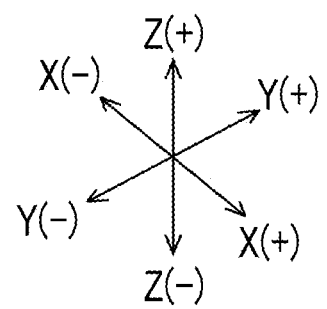

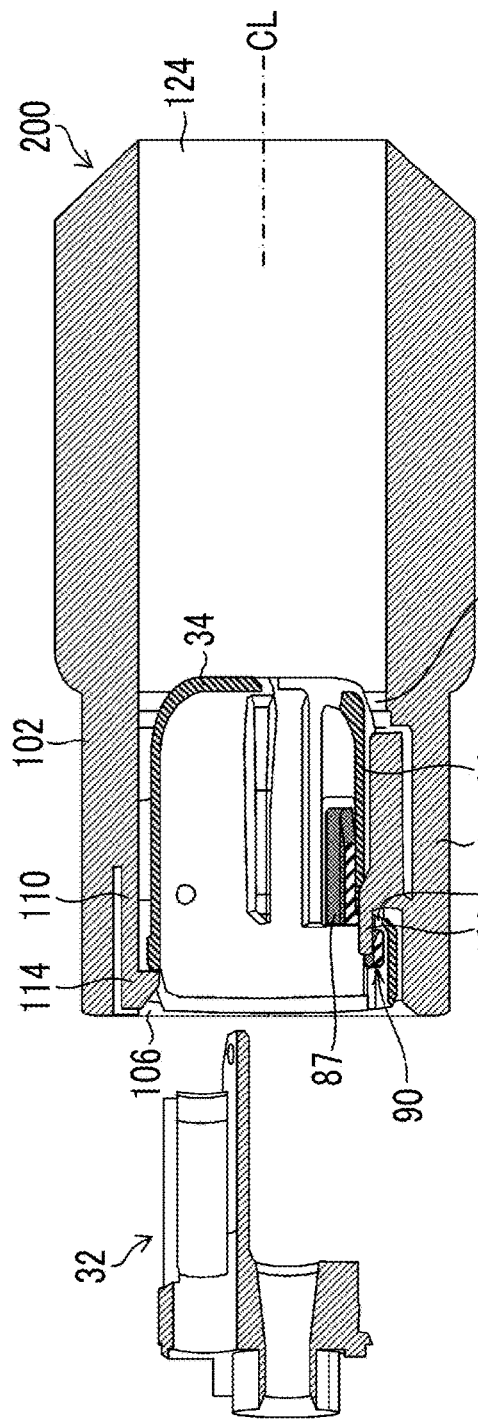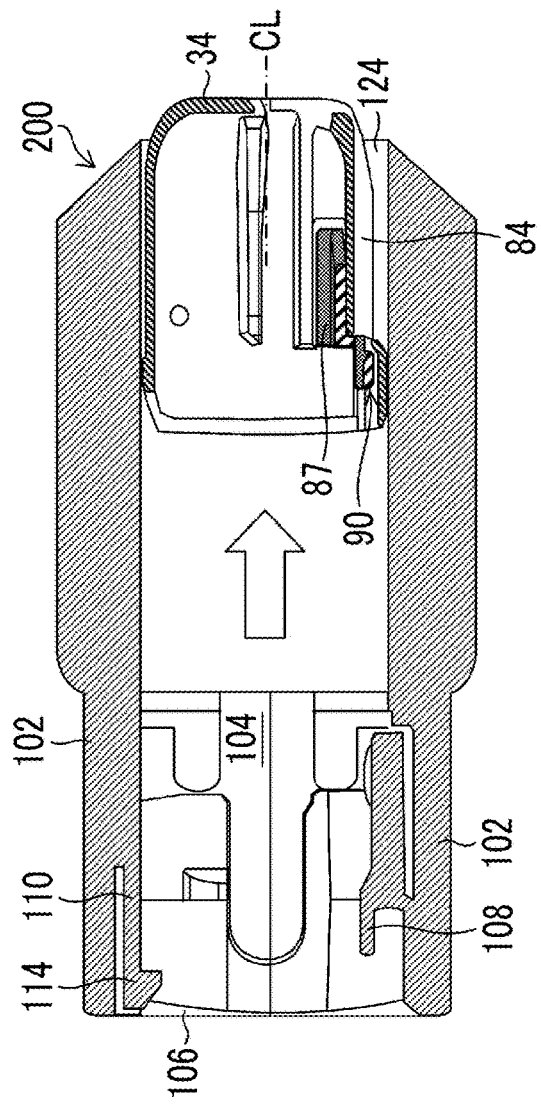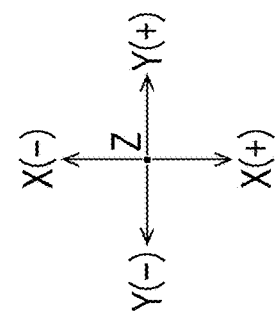

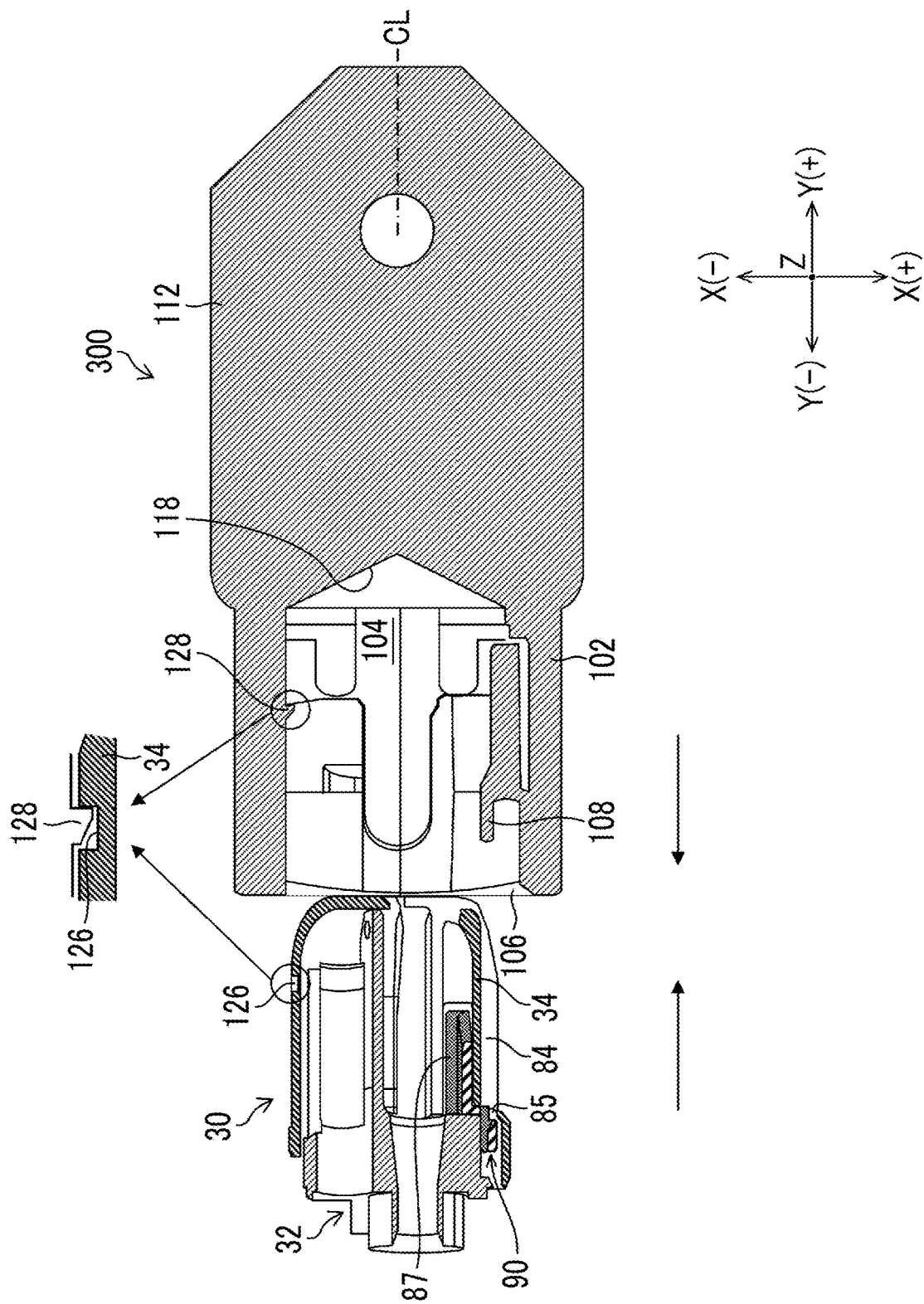

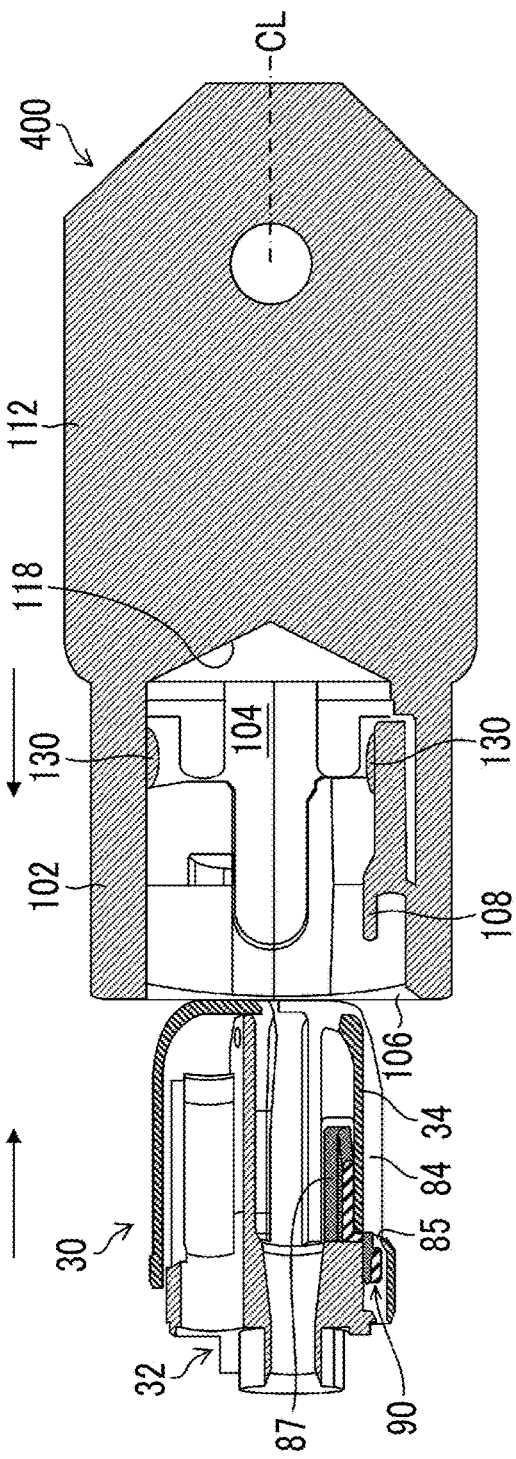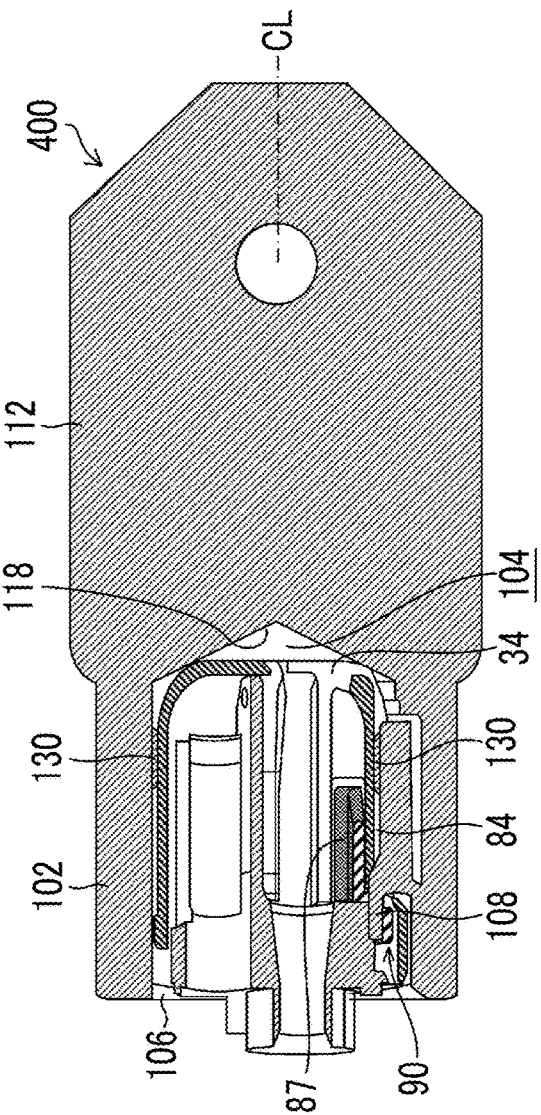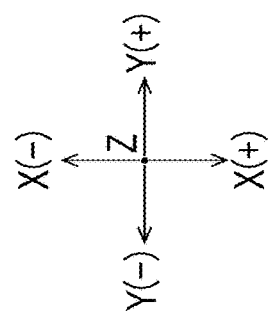

DISTAL END CAP DETACHMENT JIG AND ENDOSCOPE

CROSS-REFERENCE TO RELATED APPLICATION

The present application claims priority under 35 U.S.C § 119(a) to Japanese Patent Application No. 2021-086948 filed on May 24, 2021, which is hereby expressly incorporated by reference, in its entirety, into the present application.

BACKGROUND OF THE INVENTION

1. Field of the Invention

The present invention relates to a distal end cap detachment jig that is used to detach a distal end cap mounted on a distal end portion body of an endoscope and an endoscope comprising the distal end cap detachment jig.

2. Description of the Related Art

In an endoscope, various treatment tools are led in from a treatment tool inlet port provided on an operation part, and the treatment tools are led out to the outside from a treatment tool outlet port that is open at a distal end portion of an insertion part and are used for treatment. For example, a treatment tool such as a guide wire or a contrast tube is used in a duodenal endoscope. A treatment tool such as a puncture needle is used in ultrasonic endoscope. A treatment tool such as forceps or a snare is used in other forward-viewing endoscopes and oblique-viewing endoscopes. The lead-out direction of such a treatment tool needs to be changed in the distal end portion, in order to perform treatment at a desired position in an object to be examined. For this purpose, a distal end portion body of the distal end portion is provided with a treatment tool elevator that changes the lead-out direction of the treatment tool. The endoscope is provided with a treatment tool elevating mechanism that changes the orientation of the treatment tool elevator between an elevating position and a lying position.

Since the endoscope needs to be washed after the treatment, a distal end cap is attachably and detachably mounted on the distal end portion body and the distal end cap is detached using a jig or the like after the treatment, thereby improving washability.

For example, in JP3283135B, when a distal end cap is detached from a distal end portion body, a detachment jig is first engaged with a recess formed on the outer peripheral surface of the distal end cap from a direction orthogonal to the major axis direction of an endoscope. Next, only the distal end portion body is pulled out rearward, and the distal end cap is detached from the distal end portion body.

In WO2018/051626A, when a distal end cap is detached from a distal end portion body, first, a detachment jig is mounted so as to cover the periphery of the distal end cap and a protrusion portion of the detachment jig is inserted into a recessed portion of the distal end cap. Next, the detachment jig is rotated to make a fragile portion of the distal end cap to be broken. The detachment jig is pulled out from the distal end cap, and the broken distal end cap is detached from the distal end portion body.

SUMMARY OF THE INVENTION

However, in the case of the methods of pulling out the distal end portion body or inserting and rotating the jig to make the distal end cap to be broken when the distal end cap is detached from the distal end portion body, the operation may be difficult due to slip or it is necessary to detach the distal end cap while paying close attention so as not to spatter body fluid adhering to the endoscope. In addition, it is also conceivable that a large load is applied to the endoscope in order to avoid such a state.

The present invention has been made in view of such a circumstance, and an object thereof is to provide a distal end cap detachment jig and an endoscope capable of simply and easily detaching a distal end cap from a distal end portion body.

There is provided a distal end cap detachment jig of a first aspect that is used to detach, from a distal end portion body of an endoscope insertion part, a distal end cap which is attachable to and detachable from the distal end portion body and which is provided with a locking portion for mounting capable of being locked to the distal end portion body when the distal end cap is mounted on the distal end portion body, the distal end cap detachment jig comprising: a jig body having an accommodation space portion of which one end is provided with an opening portion; a locking release portion provided in the jig body; and a holding portion provided in the jig body, in which in a case where the distal end cap is accommodated in the accommodation space portion, the locking release portion is in a locking release state in which locking of the locking portion with respect to the distal end portion body is released and the holding portion is in a holding state in which the distal end cap is held by the holding portion, to make the distal end cap integral with the jig body so that the distal end cap is capable of being pulled out from the distal end portion body.

In the distal end cap detachment jig of a second aspect, the jig body has a bottom portion that closes the accommodation space portion and that is provided on a side of the other end opposite to the one end.

In the distal end cap detachment jig of a third aspect, the jig body has an open portion that is open to the accommodation space portion and that is provided on a side of the other end opposite to the one end.

In the distal end cap detachment jig of a fourth aspect, the open portion is formed in a size that allows the distal end cap pulled out from the distal end portion body to be discharged to an outside from the accommodation space portion.

In the distal end cap detachment jig of a fifth aspect, the distal end cap has a guide portion, the jig body has a guided portion that is capable of being engaged with the guide portion, and when the distal end cap is accommodated in the accommodation space portion, the guided portion is engaged with the guide portion and is guided so that the locking release portion and the locking portion are aligned with each other.

In the distal end cap detachment jig of a sixth aspect, the jig body has a restriction portion that restricts the distal end cap from being inserted from a circumferentially wrong direction.

In the distal end cap detachment jig of a seventh aspect, the holding portion is caught on the distal end cap.

In the distal end cap detachment jig of an eighth aspect, the holding portion is engaged with the distal end cap by a snap-fit.

In the distal end cap detachment jig of a ninth aspect, the holding portion grips the distal end cap.

In the distal end cap detachment jig of a tenth aspect, the jig body has an indicator indicating an accommodation direction of the distal end cap with respect to the accommodation space portion.

In the distal end cap detachment jig of an eleventh aspect, the jig body is a disposable.

In the distal end cap detachment jig of a twelfth aspect, a positional relationship between the locking release portion and the holding portion is a positional relationship in which the release of the locking between the distal end cap and the distal end portion body by the locking release portion and the holding of the distal end cap by the holding portion are performed at the same time, or in which the release of the locking between the distal end cap and the distal end portion body by the locking release portion is performed first and the holding of the distal end cap by the holding portion is performed later.

There is provided an endoscope of a thirteenth aspect comprising: an operation part that is provided with an operation member; an endoscope insertion part that is provided on a distal end side of the operation part and is inserted into an object to be examined; a distal end portion body that is provided on a distal end side of the endoscope insertion part; a distal end cap that is attachable to and detachable from the distal end portion body and is provided with a locking portion for mounting capable of being locked to the distal end portion body when the distal end cap is mounted on the distal end portion body; and a mounting component that is attachably and detachably mounted on the operation part, in which the mounting component includes the above-described distal end cap detachment jig.

With the distal end cap detachment jig and the endoscope of the aspects of the present invention, it is possible to simply and easily detach the distal end cap from the distal end portion body.

BRIEF DESCRIPTION OF THE DRAWINGS

FIG. 5 is a perspective view of the distal end cap from which the operation wire is detached, as viewed from a proximal end side.

FIG. 9 is a view of the distal end cap and the distal end portion body in the state of FIG. 8 as viewed from a Z(+) direction.

FIG. 21 is a view illustrating a function of the restriction portion.

FIGS. 22A and 22B are cross-sectional views illustrating a procedure for detaching the distal end cap according to a second embodiment of the distal end cap detachment jig.

FIG. 23 is a cross-sectional view illustrating a procedure for detaching the distal end cap according to a third embodiment of the distal end cap detachment jig.

FIGS. 24A and 24B are cross-sectional views illustrating a procedure for detaching the distal end cap according to a fourth embodiment of the distal end cap detachment jig.

DESCRIPTION OF THE PREFERRED EMBODIMENTS

Overall Configurations of Endoscope and Endoscope System

Figure 1:
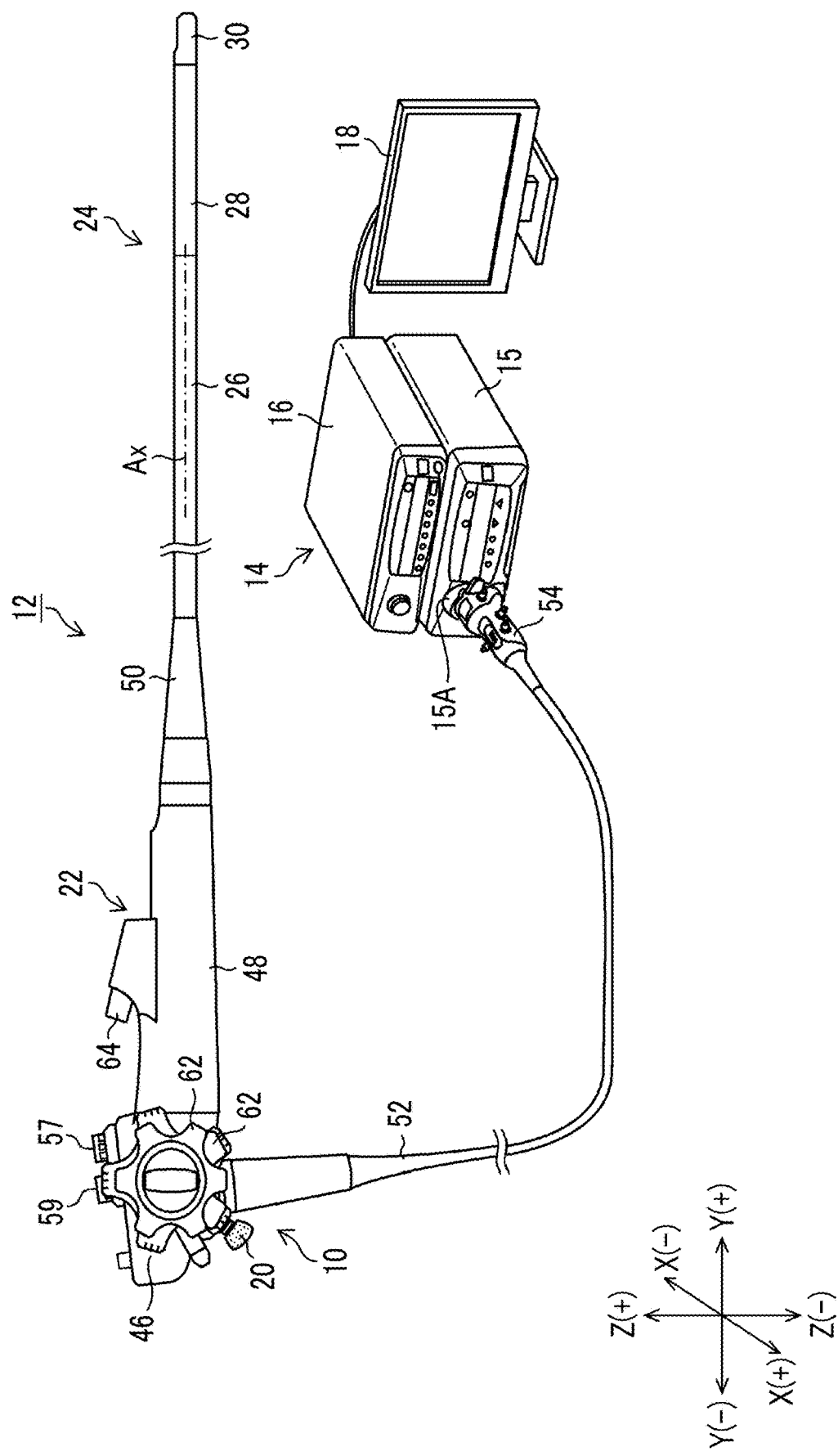
FIG. 1 is a configuration view of an endoscope system.

FIG. 1 is a configuration view of an endoscope system 12 comprising an endoscope 10. The endoscope system 12 comprises the endoscope 10, an endoscope processor apparatus 14, and a display 18.

The endoscope 10 is a side-viewing endoscope that is used as, for example, a duodenal endoscope. The endoscope 10 comprises an operation part 22 provided with an elevating operation lever 20 and an endoscope insertion part 24 connected to the operation part 22 and inserted into an object to be examined. The elevating operation lever 20 corresponds to the operation member.

The endoscope insertion part 24 is inserted into the object to be examined through the oral cavity, and further inserted from the esophagus to the duodenum by way of the stomach. With this, treatment such as a predetermined examination or treatment of the duodenum is performed using a treatment tool (not shown, the same applies hereinafter) inserted into the endoscope insertion part 24. Examples of the treatment tool may include biopsy forceps of which the distal end portion has a cup capable of collecting body tissue, a knife for endoscopic sphincterotomy (EST), or a contrast tube.

The endoscope insertion part 24 has a major axis direction Ax from the proximal end side to the distal end side thereof, and comprises a soft portion 26, a bendable portion 28, and a distal end portion 30 in this order from the proximal end side to the distal end side. The detailed configuration of the distal end portion 30 will be described later, but a schematic configuration of the distal end portion 30 will be described first.

Figure 2:
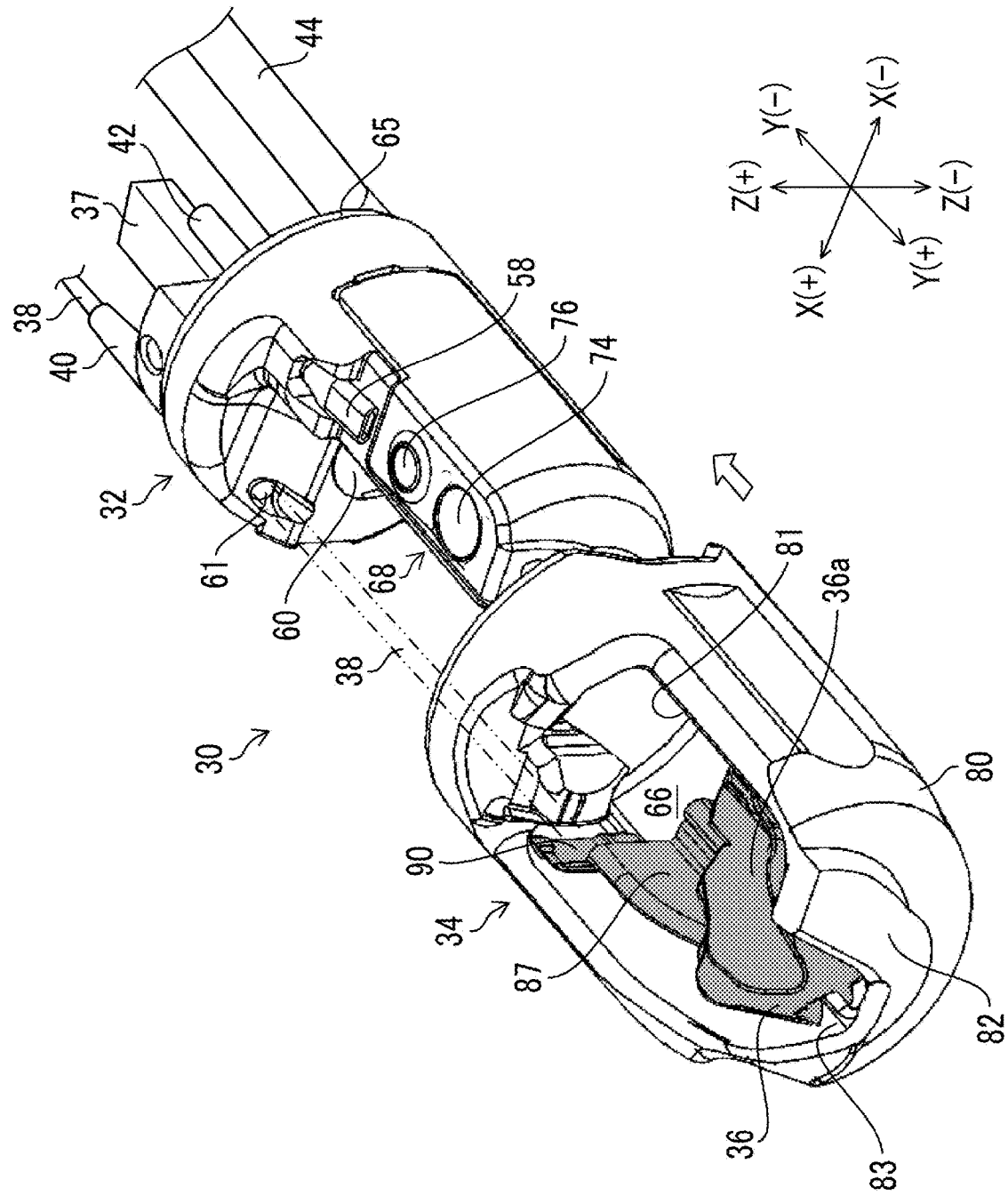
FIG. 2 is an exploded perspective view of an insertion part distal end portion.
Figure 3:
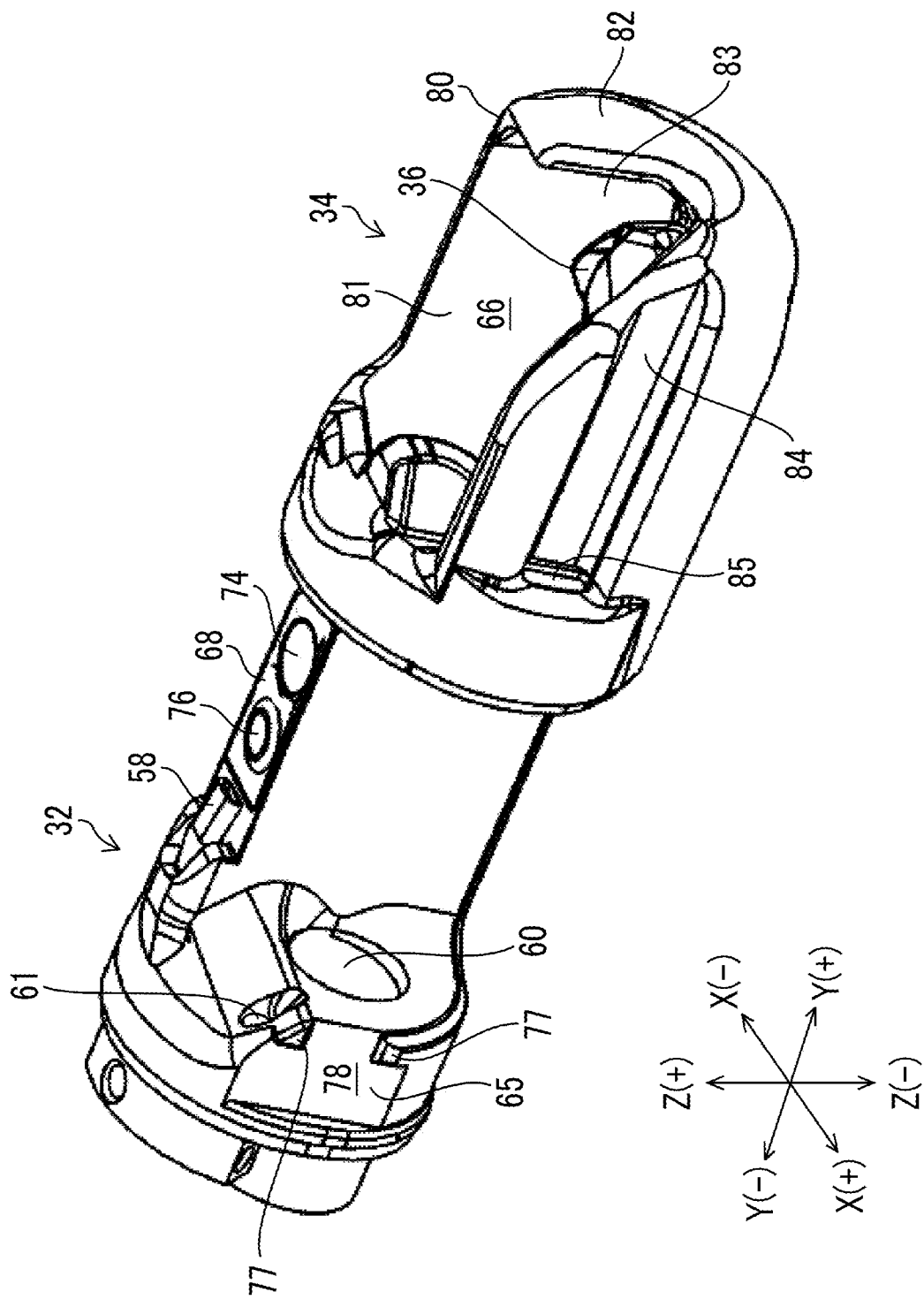
FIG. 3 is an exploded perspective view of the insertion part distal end portion as viewed from an angle different from that of FIG. 2.

FIG. 2 is an exploded perspective view of the distal end portion 30, and FIG. 3 is an exploded perspective view of the distal end portion 30 as viewed from an angle different from that of FIG. 2. As shown in FIGS. 2 and 3, the distal end portion 30 is constituted of a distal end portion body 32 and a distal end cap 34 that is attachably and detachably attached to the distal end portion body 32. In addition, the distal end portion 30 includes an elevator accommodation space 66 formed by the distal end portion body 32 and the distal end cap 34. Since FIGS. 2 and 3 are exploded perspective views, the elevator accommodation space 66 formed after the distal end cap 34 is mounted on the distal end portion body 32 is shown in the distal end cap 34. The distal end cap 34 includes a treatment tool elevator 36 (hereinafter, referred to as an elevator 36) provided so as to be rotationally movable, and the treatment tool elevator 36 has a treatment tool guide surface 36*a*. The elevator 36 is rotationally movable between the lying position and the elevating position in the elevator accommodation space 66. FIGS. 2 and 3 show a state in which the orientation of the elevator 36 is changed to the lying position.

Various contents provided inside the endoscope insertion part 24 are connected to or inserted into the distal end portion 30. Examples of the contents may include a treatment tool channel 37, an elevating operation wire 38 (hereinafter, referred to as a wire 38), a wire channel 40, an air/water supply tube 42, and a cable insertion channel 44.

The treatment tool channel 37 guides the distal end portion of the treatment tool (not shown, the same applies hereinafter), which is the distal end portion of the treatment tool, to the treatment tool outlet port 60 formed in the distal end portion body 32. The wire 38 has one end connected to the elevator 36, and rotationally moves the elevator 36 to change the lead-out direction of the treatment tool distal end portion led out from the distal end portion body 32. The wire 38 is inserted into the wire channel 40. The wire 38 and the wire channel 40 are not shown as appropriate in order to prevent the drawing from being complicated.

The air/water supply tube 42 supplies air or water supplied from the operation part 22 to an air/water supply nozzle 58 of the distal end portion body 32. A light guide that guides illumination light supplied from a light source device 15 (see FIG. 1), which will be described later, to an illumination window 74 of the distal end portion body 32, a signal cable of an imaging unit (not shown) disposed in an observation window 76, and the like are inserted into the cable insertion channel 44.

In the present specification, description will be made using a three-dimensional Cartesian coordinate system, that is, three-axis directions (an X direction, a Y direction, and a Z direction) orthogonal to each other. That is, in a case where the lead-out direction of the treatment tool (not shown) by the elevator 36 when the distal end portion 30 is viewed from the operation part 22 is set as an up direction, the up direction is a Z(+) direction and a down direction which is a direction opposite to the up direction is a Z(−) direction. In addition, in that case, a right direction is an X(+) direction and a left direction is an X(−) direction. Further, in that case, a front direction (a distal end direction of the major axis direction Ax) is a Y(+) direction and a rear direction (a proximal end direction of the major axis direction Ax) is a Y(−) direction.

Returning to FIG. 1, the soft portion 26 has a spiral tube (not shown) formed by spirally winding a thin metal strip sheet having elasticity, a tubular reticulated body (not shown) covered on the outside of the spiral tube and woven with a metal wire, and an outer cover (not shown) covered on the outer peripheral surface of the reticulated body and formed of a resin.

The bendable portion 28 comprises a structure in which a plurality of angle rings (not shown) are coupled to each other so as to be rotationally movable, a tubular metal wire reticulated body covered on the outer periphery of the structure, and a rubber outer cover covered on the outer peripheral surface of the reticulated body. For example, four angle wires (not shown) are provided from the bendable portion 28 to a pair of angle knobs 62 of the operation part 22, which will described later.

The operation part 22 has a substantially cylindrical shape as a whole. The operation part 22 has an operation part body 46 and a grip portion 48 connected to the operation part body 46. The soft portion 26 of the endoscope insertion part 24 is disposed on the distal end side of the grip portion 48 through a bending-proof pipe 50.

The grip portion 48 is gripped by an operator during the operation of the endoscope 10. The grip portion 48 is provided with a treatment tool inlet port 64 from which the treatment tool is led in. The treatment tool led in from the treatment tool inlet port 64 is led out to the outside from the treatment tool outlet port 60 (see FIGS. 2 and 3) by way of the treatment tool channel 37 (see FIG. 2).

The proximal end portion of a universal cable 52 is connected to the operation part body 46. A connector device 54 is provided at the distal end portion of the universal cable 52. The connector device 54 is connected to the endoscope processor apparatus 14.

The endoscope processor apparatus 14 comprises the light source device 15 and an image processing device 16. The light source device 15 comprises a processor-side connector 15A to which the connector device 54 is connected. Further, the display 18 that displays an image that has been subjected to image processing by the image processing device 16 is connected to the image processing device 16.

The connector device 54 and the processor-side connector 15A transmit illumination light, power, image pickup signals, and the like between the endoscope 10 and the endoscope processor apparatus 14 in a non-contact manner (wired transmission is also possible). With this, illumination light from the light source device 15 is emitted from the illumination window 74 (see FIG. 2) provided on the distal end portion body 32, through the light guide (an optical fiber cable, not shown). Further, the image pickup signal of the image picked up by the imaging unit (not shown) in the observation window 76 is subjected to image processing by the image processing device 16, and then is displayed as an image on the display 18.

The operation part body 46 is provided with an air/water supply button 57, a suction button 59, the pair of angle knobs 62, and the elevating operation lever 20.

The air/water supply button 57 is a button that can be pressed in two stages and is connected to the air/water supply tube 42 and an air/water supply source (not shown). In a case where the air/water supply button 57 is pressed in the first stage, air from the air/water supply source is ejected from the air/water supply nozzle 58 by way of the air/water supply tube 42. Further, in a case where the air/water supply button 57 is pressed in the second stage, water from the air/water supply source is ejected from the air/water supply nozzle 58 by way of the air/water supply tube 42.

The suction button 59 is connected to the treatment tool channel 37 (see FIG. 2) and a negative pressure source (not shown). In a case where the suction button 59 is pressed, air is sucked from the treatment tool outlet port 60 (see FIG. 2) by way of the treatment tool channel 37 by the negative pressure source. With this, body fluid such as blood can be sucked from the treatment tool outlet port 60.

The pair of angle knobs 62 are coaxially provided in the operation part body 46 so as to be rotationally movable. The pair of angle knobs 62 are coupled to the proximal end portion of each angle wire (not shown), which is the side opposite to the distal end portion coupled to the bendable portion 28. The pair of angle knobs 62 each are rotationally moved to push and pull each angle wire, whereby the bendable portion 28 is bent upward, downward, leftward, and rightward.

The elevating operation lever 20 is provided coaxially with the pair of angle knobs 62 in the operation part body 46 so as to be rotationally movable, and is rotationally moved by the hand of the operator who grips the grip portion 48. The elevating operation lever 20 is coupled to the proximal end portion of the wire 38, which is the side opposite to the distal end portion coupled to the elevator 36, through a link mechanism (not shown). With this, the elevating operation lever 20 is rotationally moved to push and pull the wire 38, whereby the orientation of the elevator 36 is changed between the lying position and the elevating position (see FIGS. 2 and 3).

Configuration of Distal End Portion

Next, the detailed structure of the distal end portion 30 will be described. As described above, the distal end portion 30 is constituted of the distal end portion body 32 and the distal end cap 34 that is attachably and detachably attached to the distal end portion body 32. The distal end cap 34 comprises the elevator 36 integrally formed with the wire 38.

Distal End Portion Body

As shown in FIGS. 2 and 3, the distal end portion body 32 is formed in a substantially L shape when viewed from the Z(+) direction side, and comprises a proximal end wall portion 65 and a partition wall 68.

The partition wall 68 and the air/water supply nozzle 58 are provided on the distal end surface side of the distal end portion body 32 on the Y(+) direction side. Further, the treatment tool channel 37, the wire channel 40, the air/water supply tube 42, and the cable insertion channel 44 described above are connected to the proximal end surface side of the distal end portion body 32 on the Y(−) direction side. Furthermore, various through-holes penetrating the distal end portion body 32 in the Y direction, for example, the treatment tool outlet port 60 and a wire insertion hole 61 are formed in the distal end portion body 32.

The treatment tool outlet port 60 is open in the elevator accommodation space 66, and the treatment tool channel 37 is connected thereto. With this, the treatment tool is led out from the treatment tool outlet port 60 to the outside by way of the elevator accommodation space 66 and the elevator 36.

The wire insertion hole 61 is formed at a position shifted from the treatment tool outlet port 60 to the X(+) direction side and the Z(+) direction side, and the wire 38 is inserted thereinto.

The partition wall 68 is provided on the distal end surface side of the distal end portion body 32 at a position on the X(−) direction side perpendicular to the major axis (the major axis direction Ax, the Y direction) of the distal end portion body 32 with respect to the treatment tool outlet port 60, and has a shape extending to the Y(+) direction side that is the distal end side of the distal end portion body 32.

The partition wall 68 forms the elevator accommodation space 66 for accommodating the elevator 36 (either complete accommodation or partial accommodation is possible), together with the distal end cap 34. Further, the illumination window 74 and the observation window 76 are adjacent to each other in the Y direction and are provided on the upper surface of the partition wall 68 on the Z(+) direction side.

An emission end of the above-described light guide is disposed on the inner side of the illumination window 74. With this, the illumination window 74 can illuminate the open side of the elevator accommodation space 66, that is, the Z(+) direction side of the elevator accommodation space 66.

The imaging unit (not shown) is provided on the inner side of the observation window 76. The imaging unit images a subject that exists on the Z(+) direction side of the elevator accommodation space 66 through the observation window 76. The imaging unit comprises, for example, an imaging optical system (not shown), and a complementary metal oxide semiconductor (CMOS) type or charge coupled device (CCD) type image pickup element (not shown). The image pickup signal of the subject, which is output from the image pickup element, is input to the image processing device 16 by way of the signal cable (not shown), the connector device 54, and the processor-side connector 15A. With this, the image of the subject is displayed on the display 18.

The air/water supply nozzle 58 is provided at a position on the distal end surface side of the distal end portion body 32 and on the Z(+) direction side of the partition wall 68, and jets air and water toward the observation window 76.

As shown in FIG. 3, the proximal end wall portion 65 of the distal end portion body 32 has two stopper portions 77 formed in the X(+) direction on the side opposite to the partition wall 68. The two stopper portions 77 are disposed along the Z direction. A groove portion 78 is defined by the two stopper portions 77.

The locking portion 90 provided in the distal end cap 34, which will be described later, is locked to the two stopper portions 77. The stopper portions 77 each includes a plane formed on the Y(−) direction side and substantially orthogonal to the Y direction. Meanwhile, the stopper portions 77 each includes an inclined surface formed on the Y(+) direction side such that the locking portion 90 can easily go over the stopper portions 77 when the distal end cap 34 is mounted on the distal end portion body 32.

Distal End Cap

Figure 4:
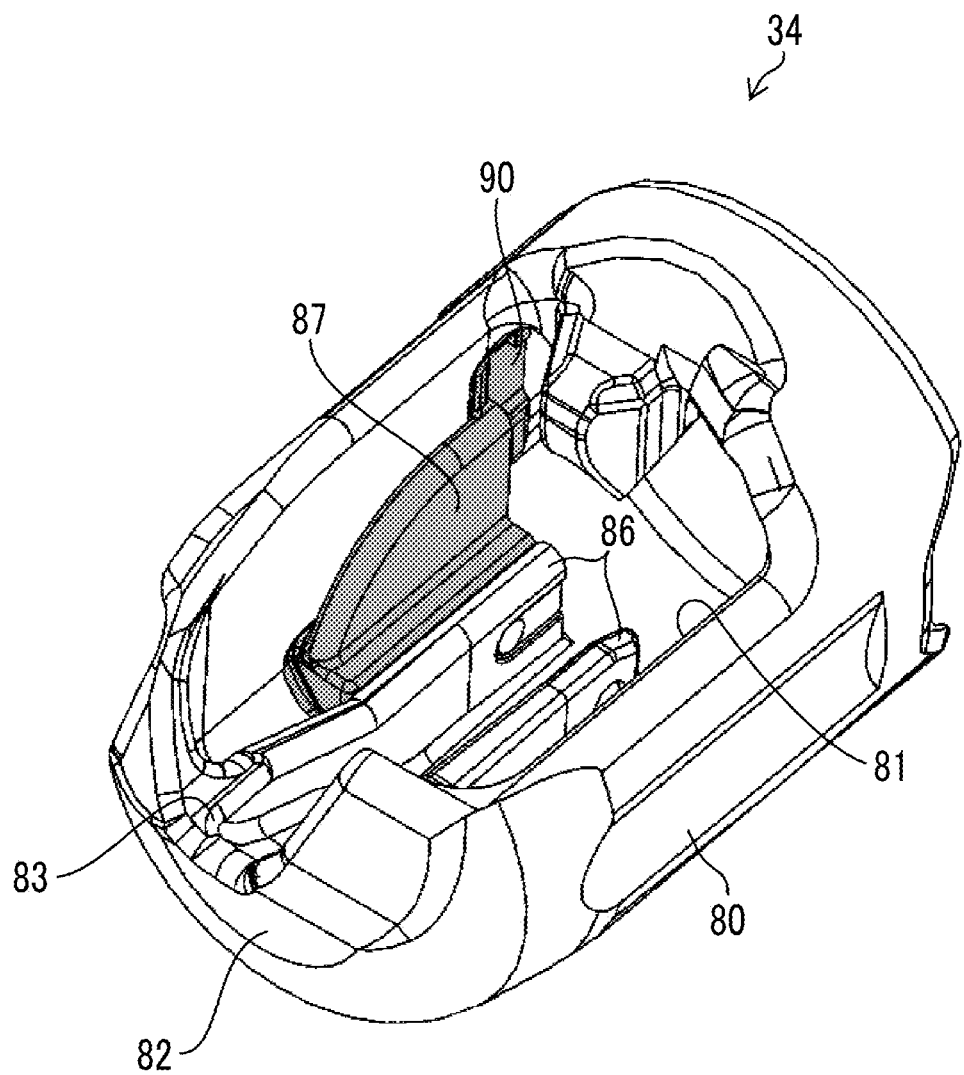
FIG. 4 is a perspective view of a distal end cap from which a treatment tool elevator and an operation wire are detached.

FIG. 4 is a perspective view of the distal end cap 34 from which the elevator 36 and the wire 38 are detached. FIG. 5 is a perspective view of the distal end cap 34 from which the wire 38 is detached, as viewed from the proximal end side.

As shown in FIGS. 2 to 5, the distal end cap 34, the elevator 36, and the wire 38 are attached to the distal end portion body 32 before the use of the endoscope 10 (treatment, examination, or the like). The distal end cap 34, the elevator 36, and the wire 38, which are detached from the distal end portion body 32 and discarded after the use is completed, are so-called disposables.

The distal end cap 34 has a substantially bottomed tubular shape, and is attachably and detachably attached to the distal end portion body 32. In a case where the distal end cap 34 is attached to the distal end portion body 32, the distal end cap 34 forms the elevator accommodation space 66 (see FIGS. 2 and 3) for accommodating the elevator 36, together with the proximal end wall portion 65 and the partition wall 68.

The distal end cap 34 has a body portion 80, a first opening portion 81 formed in the body portion 80, a distal end surface portion 82, a second opening portion 83, a groove portion 84, a third opening portion 85 (see FIG. 3), bearings 86, and a wall member 87 (see FIG. 4). The distal end cap 34 is made of an elastic material, for example, a resin material such as polysulfone or polycarbonate.

The body portion 80 has a substantially tubular shape, and forms a wall surrounding the treatment tool outlet port 60 and the partition wall 68.

When the distal end portion 30 is viewed from the position on the Z(+) direction side of the distal end portion 30, the first opening portion 81 exposes the elevator accommodation space 66 and the upper surface of the partition wall 68 (the illumination window 74, the observation window 76, and the like). With this, the treatment tool can be led out from the elevator accommodation space 66 to the Z(+) direction side, and the above-described subject can be illuminated and imaged.

The body portion 80 is open by the first opening portion 81. The body portion 80 does not need to be closed all around. On the other hand, the proximal end side of the body portion 80 has preferably a closed annular shape so as to circumferentially surround the distal end portion body 32.

The distal end surface portion 82 is coupled to the body portion 80 and is provided on the distal end side of the distal end cap 34 in the Y(+) direction. The distal end surface portion 82 covers the distal end surface of the distal end portion body 32 on the Y(+) direction side. The distal end surface portion 82 and the body portion 80 make the distal end cap 34 have a substantially bottomed tubular shape as a whole. The second opening portion 83 that exposes the elevator accommodation space 66 is formed in the distal end surface portion 82 when viewed from the distal end side of the distal end cap 34 (when the distal end cap 34 is viewed from a position on the Y(+) direction side of the distal end cap 34). The second opening portion 83 may not be formed.

The groove portion 84 is formed on the outer side of the body portion 80 on the X(+) direction side along the Y direction from the distal end side to the proximal end side of the distal end cap 34 (see FIG. 3). The third opening portion 85 is formed on the proximal end side (Y(−) direction side) of the groove portion 84. The third opening portion 85 is disposed at a position facing the groove portion 78 of the proximal end wall portion 65 when the distal end cap 34 is mounted on the distal end portion body 32.

The bearings 86 (see FIGS. 4 and 5) are formed on the inner peripheral surface of the distal end cap 34 that defines the bottom surface (Z(−) direction side) of the elevator accommodation space 66. The bearings 86 hold the elevator 36 such that the elevator 36 is rotationally movable between the lying position and the elevating position through a rotary shaft 88 (see FIG. 5).

As shown in FIG. 4, the wall member 87 is disposed inside the body portion 80 at a position on the X(+) direction side with respect to the bearings 86, and has a shape extending to the Y(+) direction side. The wall member 87 protrudes toward the X(−) direction side with respect to the inner peripheral surface of the body portion 80. At least a part of the wall member 87 overlaps with the track of the wire 38 (not shown) when viewed from a position on the Z(+) direction side of the distal end portion 30. That is, the wall member 87 is formed at a position where the gap on the Z(−) direction side of the track of the wire 38 is filled. With this, the wall member 87 can prevent the treatment tool distal end portion from getting into the gap.

The wall member 87 comprises the locking portion 90 that is provided on the proximal end side and that is locked to the stopper portions 77 of the proximal end wall portion 65 (see FIGS. 4 and 5). The locking portion 90 is a member for mounting that can be locked to the stopper portions 77 of the distal end portion body 32 when the distal end cap 34 is mounted on the distal end portion body 32. The locking portion 90 is disposed so as not to overlap with the third opening portion 85. The wall member 87 is fixed to the bearing 86 together with the elevator 36 by the rotary shaft 88. The wall member 87 is not exposed to the outside of the distal end cap 34 because the wall member 87 is provided on the inner peripheral surface of the body portion 80.

Figure 6:
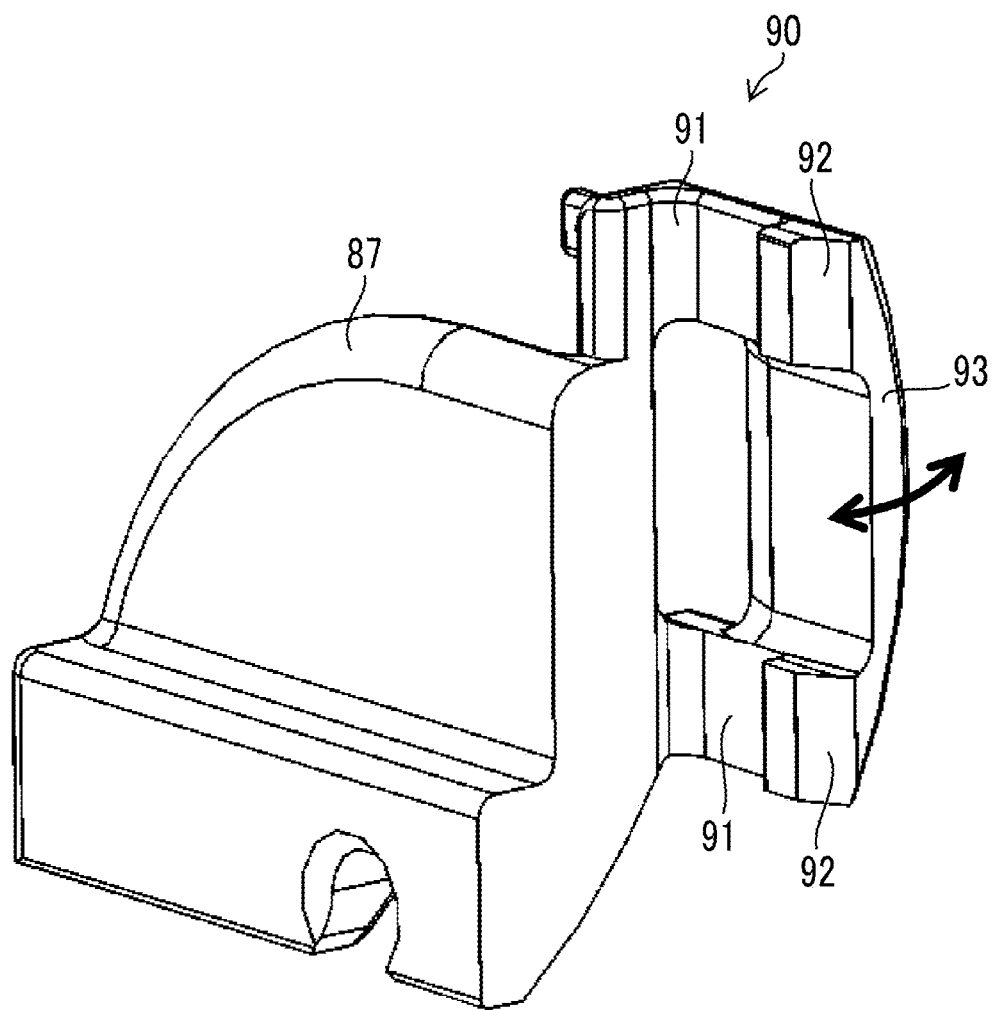
FIG. 6 is an enlarged view of a wall member and is a perspective view seen from the proximal end side.

FIG. 6 is an enlarged view of the wall member 87 and is a perspective view seen from the proximal end side. The locking portion 90 comprises two support members 91 each extending from the wall member 87 to the X(+) direction side and further extending to the Y(−) direction side, and having an L shape when viewed from the Z(+) direction side. The two support members 91 are disposed apart from each other in the Z direction so as not to overlap with the third opening portion 85 (see FIG. 5). The two support members 91 each have a claw portion 92 provided on the proximal end side thereof and extending to the X(−) direction side. The claw portions 92 each have a plane formed on the Y(+) direction side and substantially orthogonal to the Y direction. Meanwhile, the claw portions 92 each have an inclined surface that is formed on the Y(−) direction side and that is gradually inclined in the Y(−) direction, from the X(−) direction toward the X(+) direction. A coupling member 93 through which the two support members 91 are coupled is provided.

The two support members 91 are cantilevered by the wall member 87 and are elastically deformable with this support portions as fulcrums, and the two claw portions 92 are free ends and the orientation thereof can be changed in the X direction as indicated by the arrow.

Mounting Between Distal End Cap and Distal End Portion Body

Next, mounting between the distal end cap 34 and the distal end portion body 32 will be described. In FIGS. 7 to 11, for ease of understanding, the body portion 80 of the distal end cap 34 is shown by a virtual line, and the elevator 36 is not shown, as appropriate.

Figure 7:
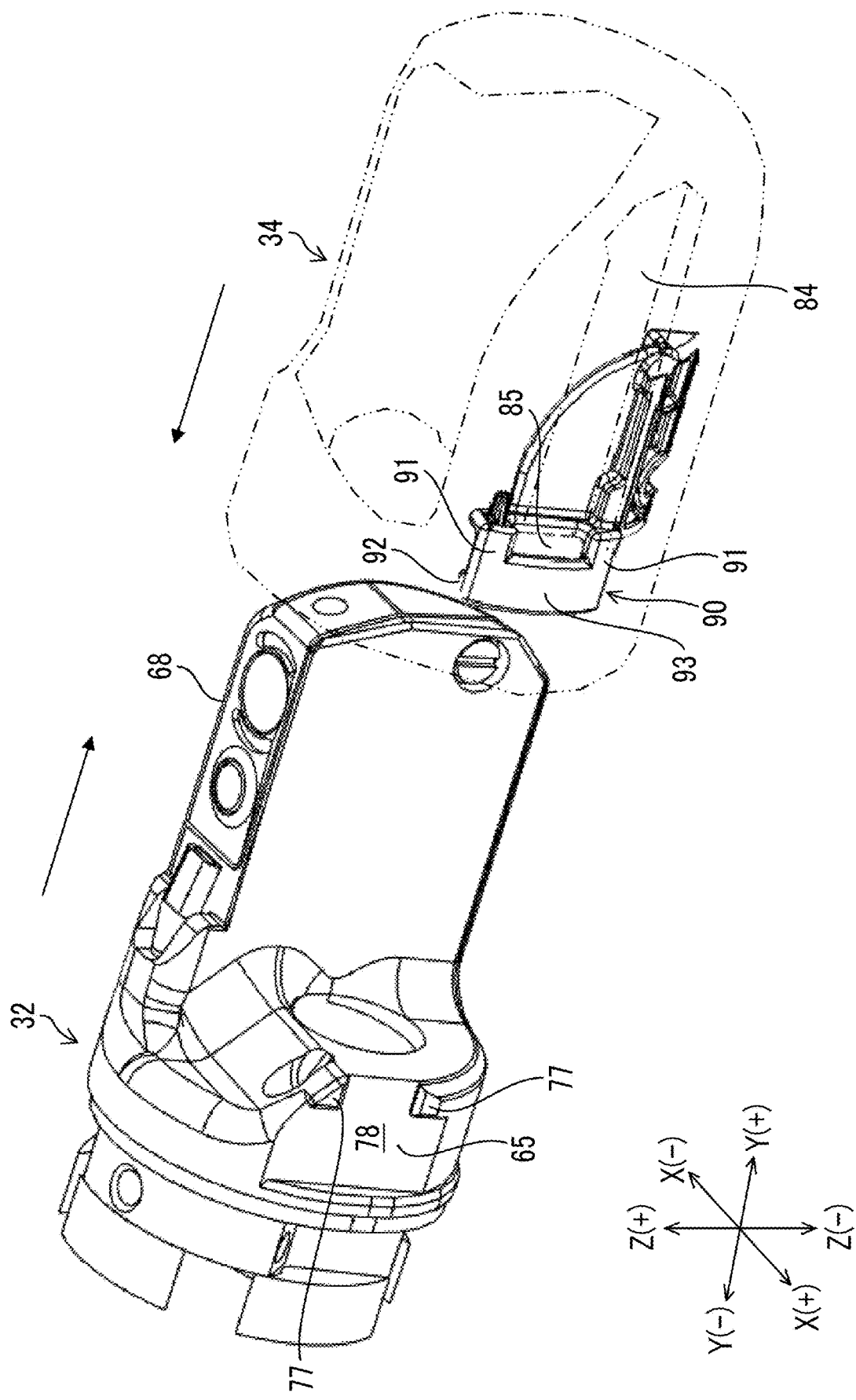
FIG. 7 is a view showing a state before the distal end cap is mounted on a distal end portion body.

FIG. 7 shows a state before the distal end cap 34 is mounted on the distal end portion body 32. When the distal end cap 34 is mounted on the distal end portion body 32, the positions of the groove portion 84 of the distal end cap 34 and the stopper portions 77 of the proximal end wall portion 65 are adjusted. Next, as indicated by the arrow, the distal end cap 34 and the distal end portion body 32 are moved in an approach direction relative to each other along the Y direction.

Figure 8:
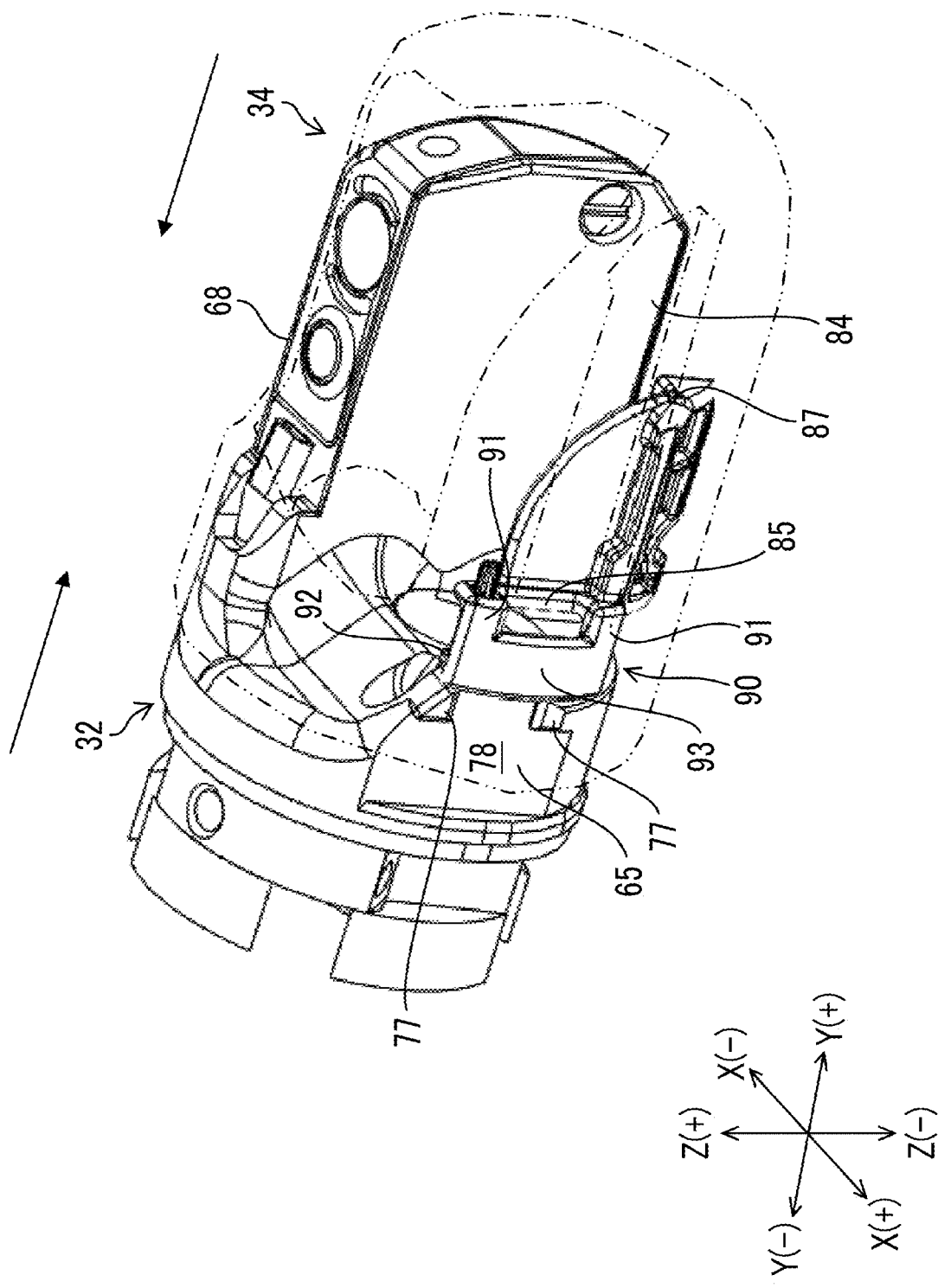
FIG. 8 is a view showing a state immediately before a locking portion of the wall member is locked to stopper portions of a proximal end wall portion.

FIG. 8 shows a state immediately before the locking portion 90 of the wall member 87 is locked to the stopper portions 77 of the proximal end wall portion 65. In a case where the distal end cap 34 and the distal end portion body 32 are brought close to each other from the state of FIG. 7, the distal end portion body 32 is accommodated in a space portion of the distal end cap 34, and the locking portion 90 and the stopper portions 77 approach a position where the locking portion 90 and the stopper portions 77 come into contact with each other, as shown in FIG. 8. FIG. 9 is a view of the distal end cap 34 and the distal end portion body 32 in the state of FIG. 8, as viewed from the Z(+) direction side. As shown in FIG. 9, the claw portions 92 of the locking portion 90 approach a position immediately before coming into contact with the stopper portions 77. The claw portions 92 of the locking portion 90 are not yet locked to the stopper portions 77. The inclined surfaces of the stopper portions 77 on the Y(+) direction side and the inclined surfaces of the claw portions 92 are at positions facing each other.

Figure 10:
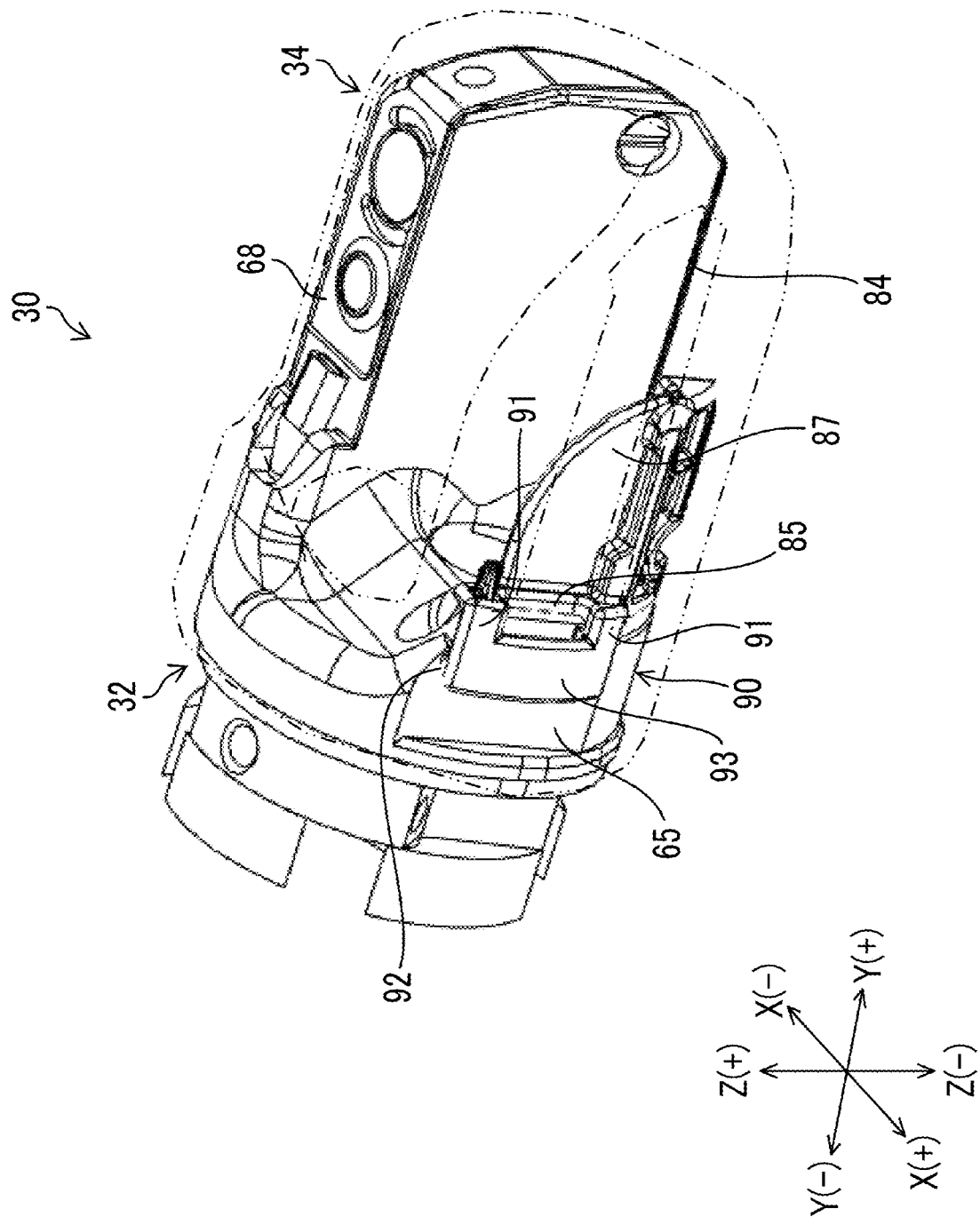
FIG. 10 is a view showing a state in which the locking portion of the wall member is locked to the stopper portions of the proximal end wall portion.
Figure 11:
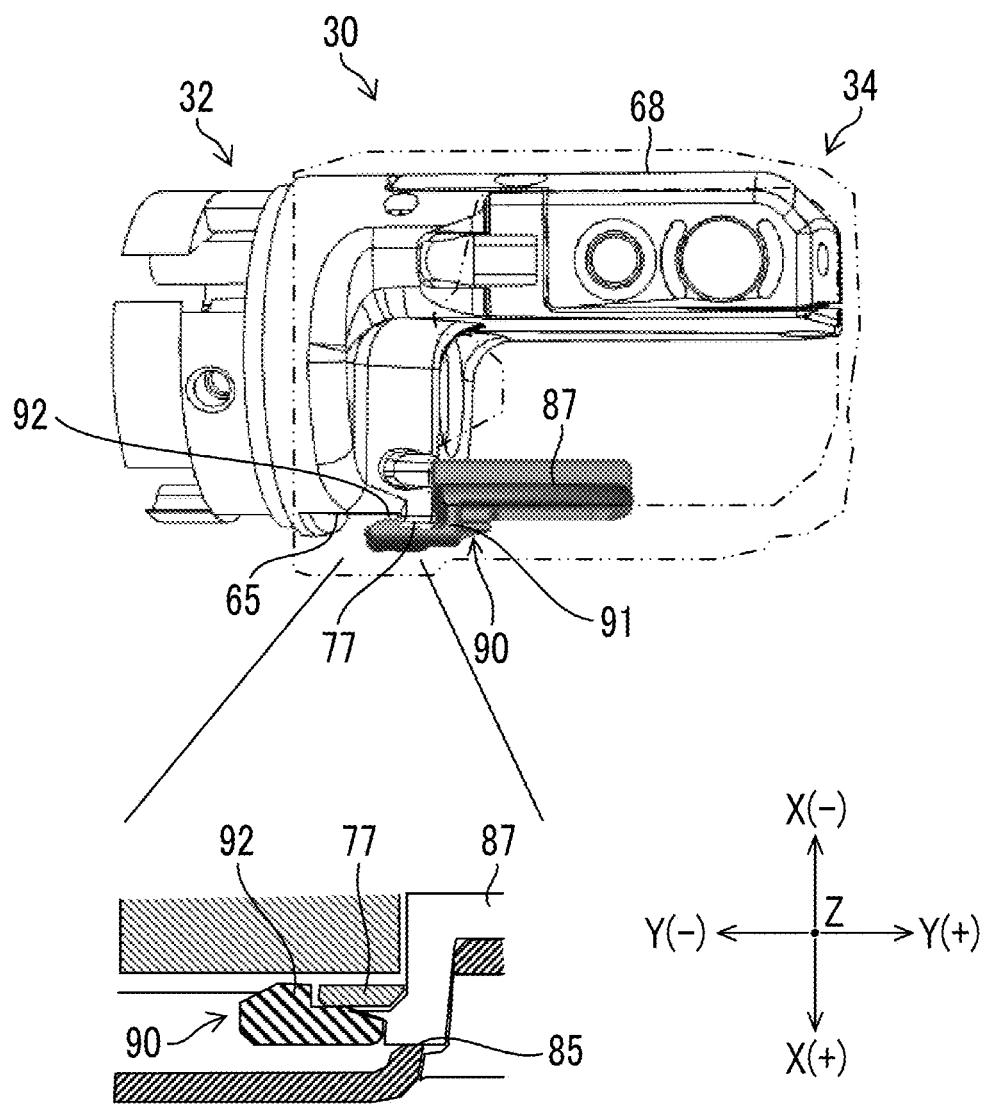
FIG. 11 is a view of the distal end cap and the distal end portion body in the state of FIG. 10 as viewed from the Z(+) direction.

FIG. 10 shows a state in which the locking portion 90 of the wall member 87 is locked to the stopper portions 77 of the proximal end wall portion 65. In a case where the distal end cap 34 and the distal end portion body 32 are brought closer to each other from the state of FIG. 9, the locking portion 90 is locked to the stopper portions 77. FIG. 11 is a view of the distal end cap 34 and the distal end portion body 32 in the state of FIG. 10, as viewed from the Z(+) direction. As the distal end cap 34 and the distal end portion body 32 are moved relative to each other along the Y direction, the claw portions 92 of the locking portion 90 and the stopper portions 77 come into contact with each other.

As described above, the claw portions 92 are provided on the cantilevered support members 91. Therefore, in a case where the distal end cap 34 is moved relative to the distal end portion body 32, the claw portions 92 are moved in the X(+) direction due to the elastic deformation of the support members 91, and the sides of the inclined surfaces of the claw portions 92 run on the inclined surfaces of the stopper portions 77. In a case where the distal end cap 34 is moved to the mounting position with respect to the distal end portion body 32, the two claw portions 92 of the locking portion 90 go over the two stopper portions 77, the elastic deformation of the support members 91 returns to the original state, and the claw portions 92 are moved in the X(−) direction. The claw portions 92 are locked to the stopper portions 77. A click feeling is generated when the claw portions 92 has gone over the stopper portions 77, so that the operator can recognize that the distal end cap 34 is mounted on the distal end portion body 32.

Since the plane on the Y(−) direction side of the stopper portion 77 and the plane on the Y(+) direction side of the claw portion 92 of the locking portion 90 are locked to each other, the distal end cap 34 is restricted from being moved to the Y(+) direction side relative to the distal end portion body 32, and the distal end cap 34 is restrained from being falling off from the distal end portion body 32. With the above-described structures of the distal end cap 34 and the distal end portion body 32, the operator can easily mount the distal end cap 34 on the distal end portion body 32.

Detachment of Distal End Cap from Distal End Portion Body

The distal end cap 34 is mounted on the distal end portion body 32, and then the distal end portion 30 of the endoscope 10 shown in FIG. 1 is inserted into the object to be examined. The treatment tool is directed in a desired lead-out direction in the object to be examined by the elevator 36 of the distal end portion 30 (see, for example, FIG. 2).

After the treatment is completed, the distal end cap 34 is detached and the distal end portion body 32 is washed. Therefore, it is required that the distal end cap 34 can be easily detached from the distal end portion body 32 and the damage or load applied to the endoscope 10 is restrained upon the detachment.

Hereinafter, a distal end cap detachment jig according to the embodiments will be described.

First Embodiment

Figure 12:
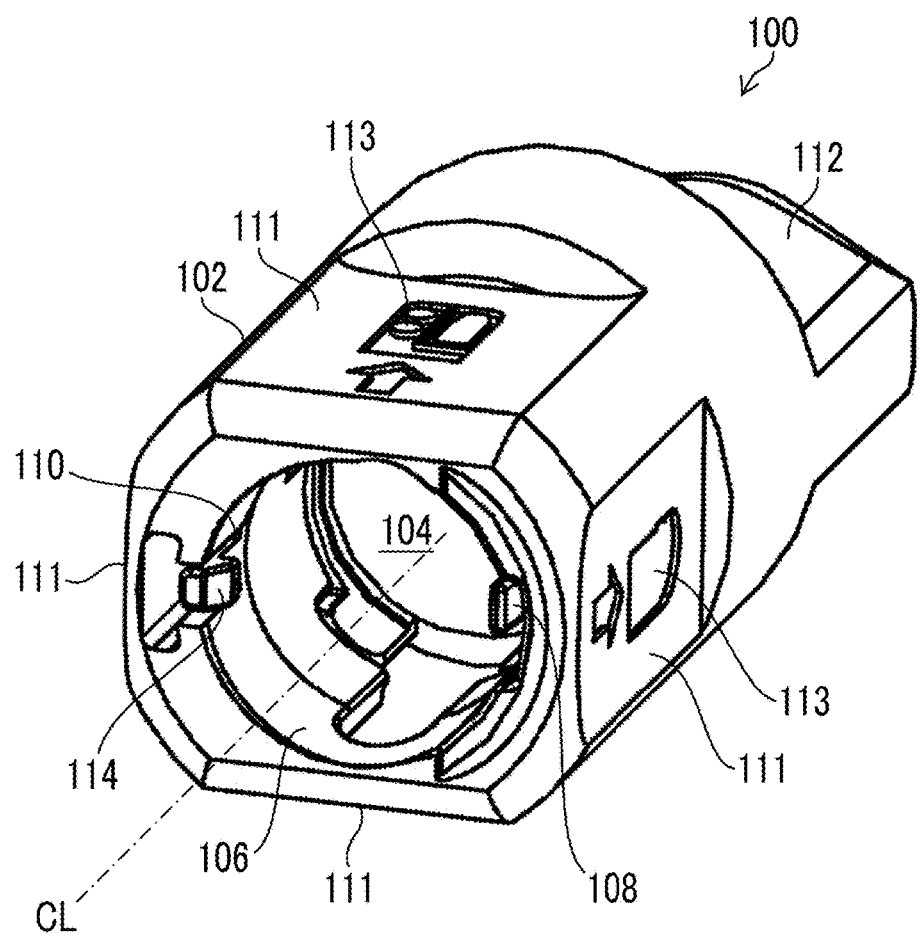
FIG. 12 is a perspective view of a distal end cap detachment jig.

FIG. 12 is a perspective view of a distal end cap detachment jig 100. As shown in FIG. 12, the distal end cap detachment jig 100 comprises a jig body 102 having an accommodation space portion 104 of which one end is provided with an opening portion 106, a locking release portion 108 provided in the jig body 102, and a holding portion 110 provided in the jig body.

The jig body 102 has a substantially cylindrical shape as a whole, and comprises four planes 111 separated from each other by about 90° with respect to a central axis CL of the jig body 102 and provided on the outer peripheral surface thereof. The planes 111 each extends along the central axis CL with the opening portion 106 as a starting point. The planes 111 provided make it easier for the operator or the like to grip the jig body 102 with his or her fingers.

It is preferable that the plane 111 has, for example, an indicator 113 indicating the accommodation direction of the distal end cap 34 with respect to the accommodation space portion 104. The indicator 113 can guide the distal end cap 34 to be inserted into the distal end cap detachment jig 100 in the correct direction. The indicator 113 is not particularly limited as long as the operator can recognize indicators such as printing and unevenness. Further, the indicator 113 is not limited to being provided on the plane 111.

The jig body 102 is provided with a plate-shaped member 112 on the side opposite to the opening portion 106.

The accommodation space portion 104 is formed inside the jig body 102, and has one end provided with the opening portion 106. The accommodation space portion 104 has a size and a shape that make it possible to accommodate the distal end cap 34 through the opening portion 106. The size and the shape of the accommodation space portion 104 can be defined by the interior wall of the jig body 102.

The locking release portion 108 is provided in the accommodation space portion 104 of the jig body 102. The locking release portion 108 releases the locking between the locking portion 90 of the distal end cap 34 and the stopper portions 77 of the distal end portion body 32 as described above when the distal end portion body 32 on which the distal end cap 34 is mounted is accommodated in the accommodation space portion 104. In a case where the locking between the distal end cap 34 and the distal end portion body 32 is released, the distal end cap 34 can be detached from the distal end portion body 32.

The holding portion 110 is provided in the accommodation space portion 104 of the jig body 102. In the state in which the locking between the distal end cap 34 and the distal end portion body 32 is released, the holding portion 110 is in a holding state in which the distal end cap is held by the holding portion. The holding portion 110 has a role of holding the distal end cap 34 in the jig body 102. Therefore, in a case where the distal end cap detachment jig 100 is moved in a direction away from the distal end portion body 32, the distal end cap 34 is integrated with the jig body 102 so that the distal end cap 34 can be pulled out from the distal end portion body 32.

In the distal end cap detachment jig 100 of FIG. 12, the locking release portion 108 and the holding portion 110 are provided at positions facing each other with the accommodation space portion 104 interposed therebetween. However, the present invention is not limited to these positions.

Figure 13:
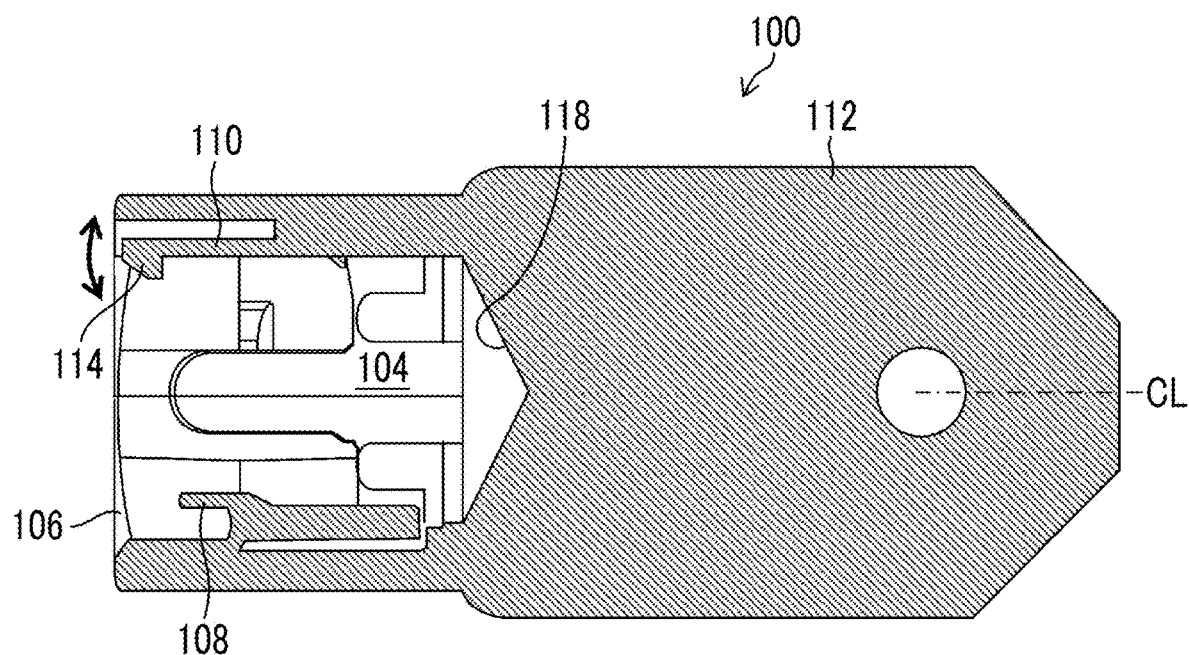
FIG. 13 is a cross-sectional view of the distal end cap detachment jig taken along a plane parallel to a central axis and passing through a locking release portion and a holding portion.

FIG. 13 is a cross-sectional view of the distal end cap detachment jig 100 taken along a plane parallel to the central axis CL and passing through the locking release portion 108 and the holding portion 110.

As shown in FIG. 13, the jig body 102 comprises the accommodation space portion 104, the locking release portion 108, the holding portion 110, and a bottom portion 118.

The locking release portion 108 is provided in the accommodation space portion 104 of the jig body 102, extends toward the opening portion 106, and has a shape that tapers toward the opening portion 106. As will be described later, the locking release portion 108 is inserted into the third opening portion 85 of the distal end cap 34 to release the locking between the distal end cap 34 and the distal end portion body 32.

The holding portion 110 is provided in the accommodation space portion 104 of the jig body 102, extends toward the opening portion 106, and comprises a claw portion 114 on the side facing the opening portion 106. The claw portion 114 protrudes toward the central axis CL. The holding portion 110 is cantilevered on the side opposite to the opening portion 106, and the orientation of the claw portion 114 can be changed in the direction indicated by the arrow as a free end due to the elastic deformation of the holding portion 110.

Further, the claw portion 114 has an inclined surface on the side of the opening portion 106 and a plane on the side opposite to the opening portion 106. The inclined surface approaches the central axis CL as the inclined surface is farther away from the opening portion 106. Meanwhile, the plane is substantially orthogonal to the central axis CL. The holding portion 110 shown in FIG. 13 has a structure that can be engaged with the distal end cap 34 by a snap-fit as will be described later.

The jig body 102 has the bottom portion 118 that closes the accommodation space portion 104 and that is provided on the side of the other end opposite to the opening portion 106 which is positioned at the one end. Only the one end of the accommodation space portion 104 is open by the opening portion 106.

Next, procedures for detaching the distal end cap 34 using the distal end cap detachment jig 100 of the first embodiment will be described with reference to FIGS. 14 to 18.

Figure 14:
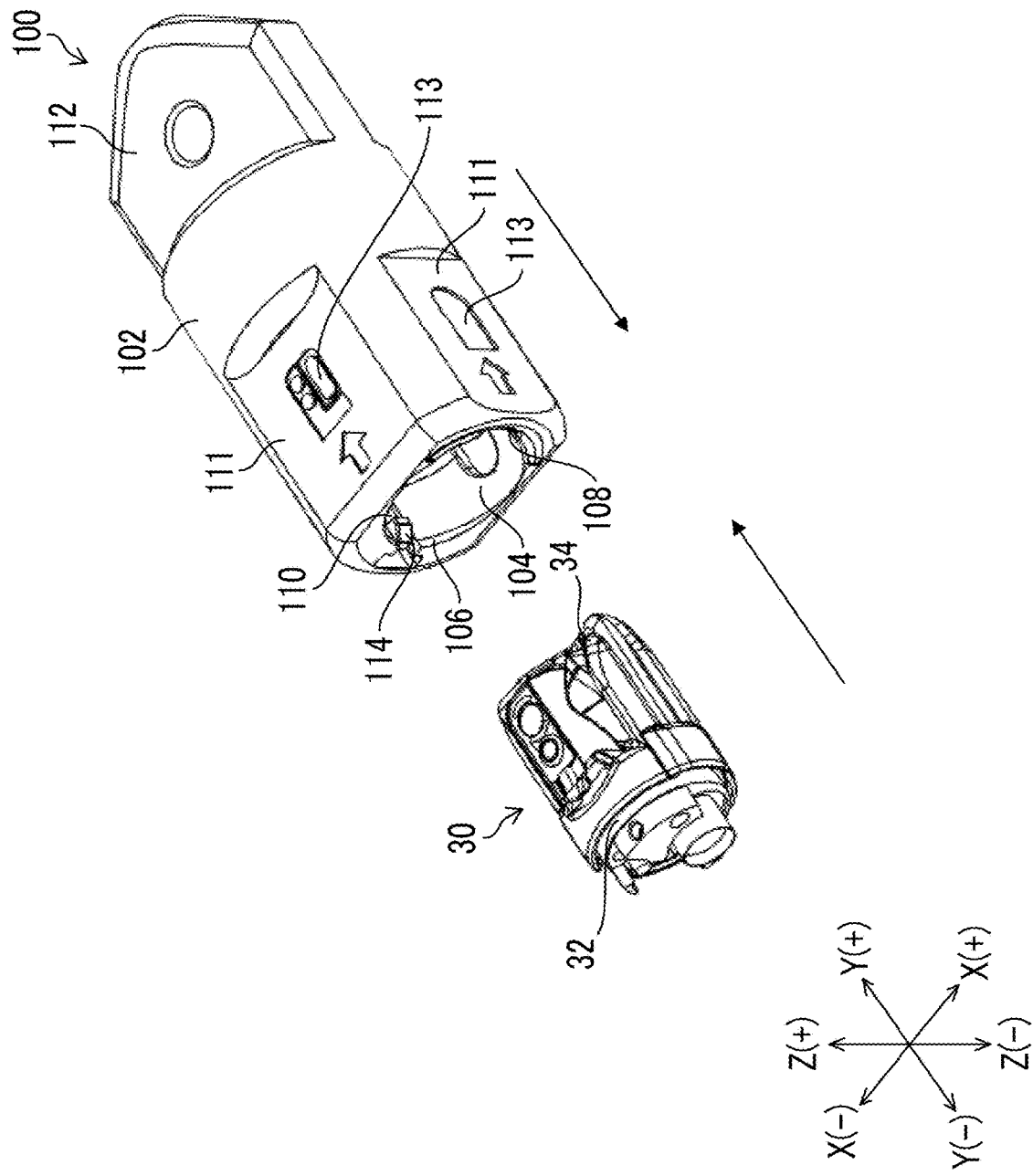
FIG. 14 is a perspective view illustrating a procedure for detaching the distal end cap according to a first embodiment of the distal end cap detachment jig.

FIG. 14 shows a state before the distal end portion 30 is inserted into the distal end cap detachment jig 100. As described above, the distal end cap 34 is mounted on the distal end portion body 32 in a state in which the locking portion 90 is locked to the stopper portions 77. The distal end portion 30 and the distal end cap detachment jig 100 are moved in an approach direction relative to each other along the Y direction as indicated by the arrow.

As shown in FIG. 14, the jig body 102 is provided with the indicator 113. The indicator 113 shows the shape of the distal end portion 30 as viewed from the Z(+) direction as a schematic view. With the indicator 113 shown as a schematic view, the insertion direction of the distal end cap detachment jig 100 with respect to the distal end portion 30 can be guided in the correct direction. Further, the indicator 113 can be provided not only at one place but also on the plane 111 as viewed from the X(+) direction.

Figure 15:
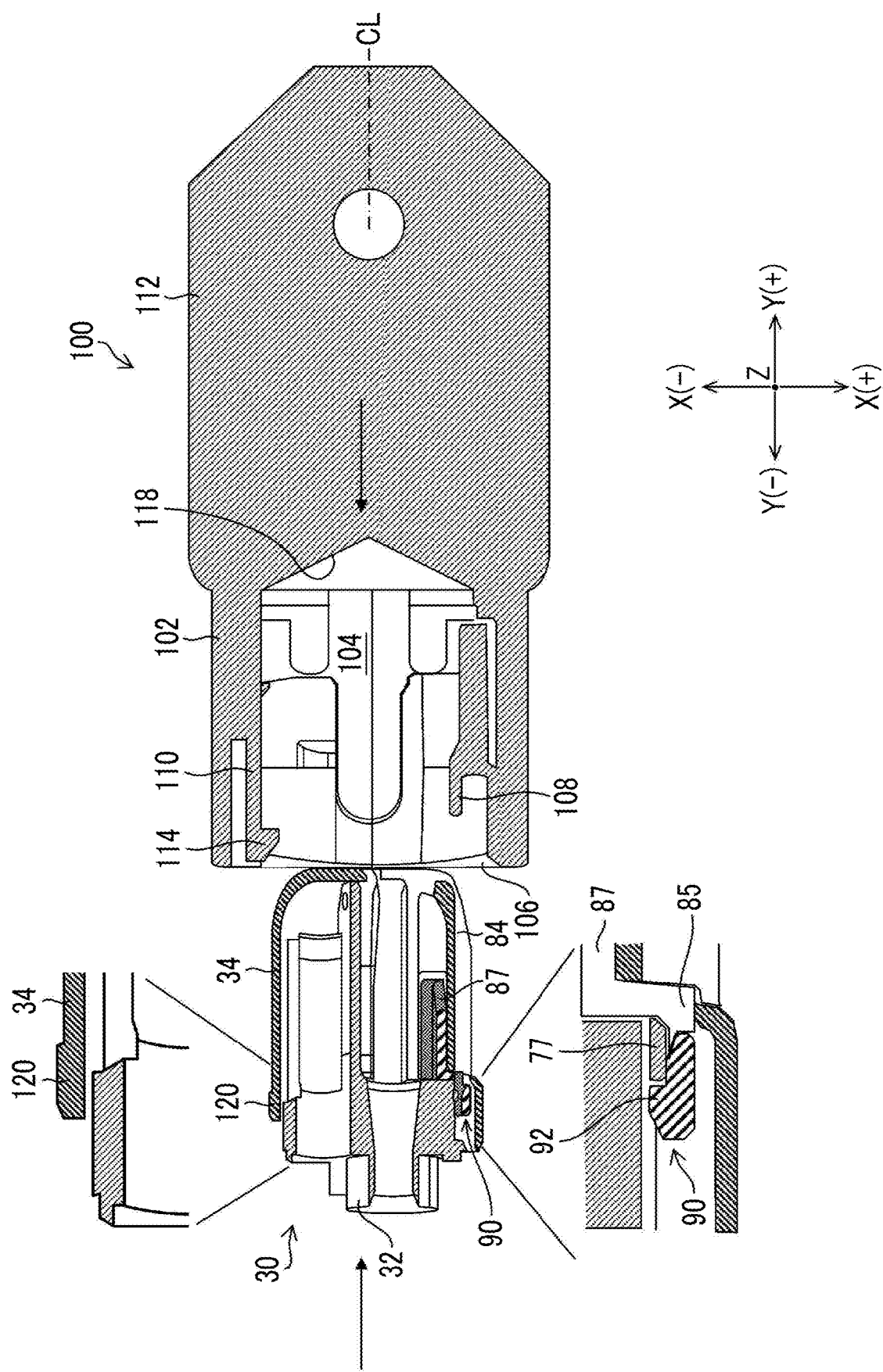
FIG. 15 is a cross-sectional view illustrating the procedure for detaching the distal end cap according to the first embodiment of the distal end cap detachment jig.

FIG. 15 is a cross-sectional view illustrating the procedure for detaching the distal end cap 34. FIG. 15 is a cross-sectional view of the distal end portion 30 and the distal end cap detachment jig 100 taken along a plane orthogonal to the Z direction and passing through the locking release portion 108 and the holding portion 110 in the state of FIG. 14. The elevator 36 and the wire 38 are not shown for ease of understanding. Since the distal end portion 30 is not yet accommodated in the jig body 102, the distal end cap 34 is mounted on the distal end portion body 32, that is, the locking portion 90 is locked to the stopper portions 77. As shown in the upper part of FIG. 15, a protruding portion 120 is provided at the end portion of the distal end cap 34 on the proximal end side so that the claw portion 114 of the holding portion 110 can be easily engaged by the snap-fit.

Figure 16:
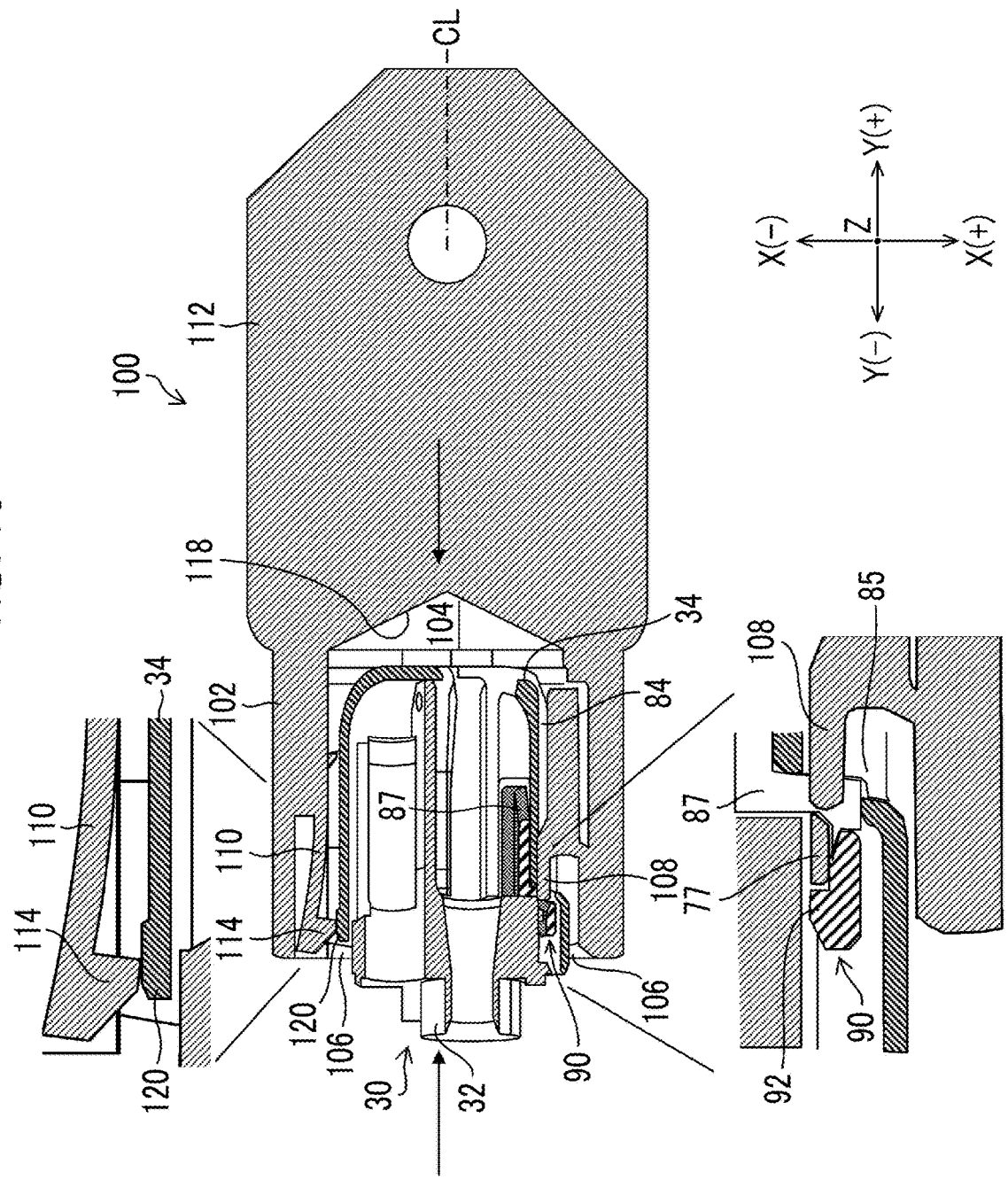
FIG. 16 is a cross-sectional view illustrating the procedure for detaching the distal end cap according to the first embodiment of the distal end cap detachment jig.

FIG. 16 shows a state immediately before the locking release portion 108 releases the locking between the distal end cap 34 and the distal end portion body 32 in a state in which the distal end cap 34 of the distal end portion 30 is accommodated in the accommodation space portion 104 of the jig body 102.

As described above, the distal end cap 34 is provided with the groove portion 84 along the Y direction. As shown in the lower part of FIG. 16, in a case where the distal end portion 30 is inserted into the distal end cap detachment jig 100 in a state in which the circumferential angles of the distal end portion 30 and the distal end cap detachment jig 100 substantially match with each other, the locking release portion 108 is slidably engaged with the groove portion 84 of the distal end cap 34 and is moved toward the third opening portion 85 along the groove portion 84. With this, the positions of the distal end portion 30 and the distal end cap detachment jig 100 are finely adjusted, and the alignment is performed while guiding the distal end cap detachment jig 100. The groove portion 84 of the distal end cap 34 functions as a guide portion, and the locking release portion 108 functions as a guided portion. Although the case where the locking release portion 108 also serves as the guided portion has been described, a guided portion can be provided separately from the locking release portion 108. The locking release portion 108 is guided to the third opening portion 85 as shown in the lower part of FIG. 16.

As shown in the upper part of FIG. 16, in a case where the holding portion 110 and the distal end cap 34 come into contact with each other, the holding portion 110 is elastically deformed in the X(−) direction and is moved toward the protruding portion 120 along the outer peripheral surface of the distal end cap 34.

Figure 17:
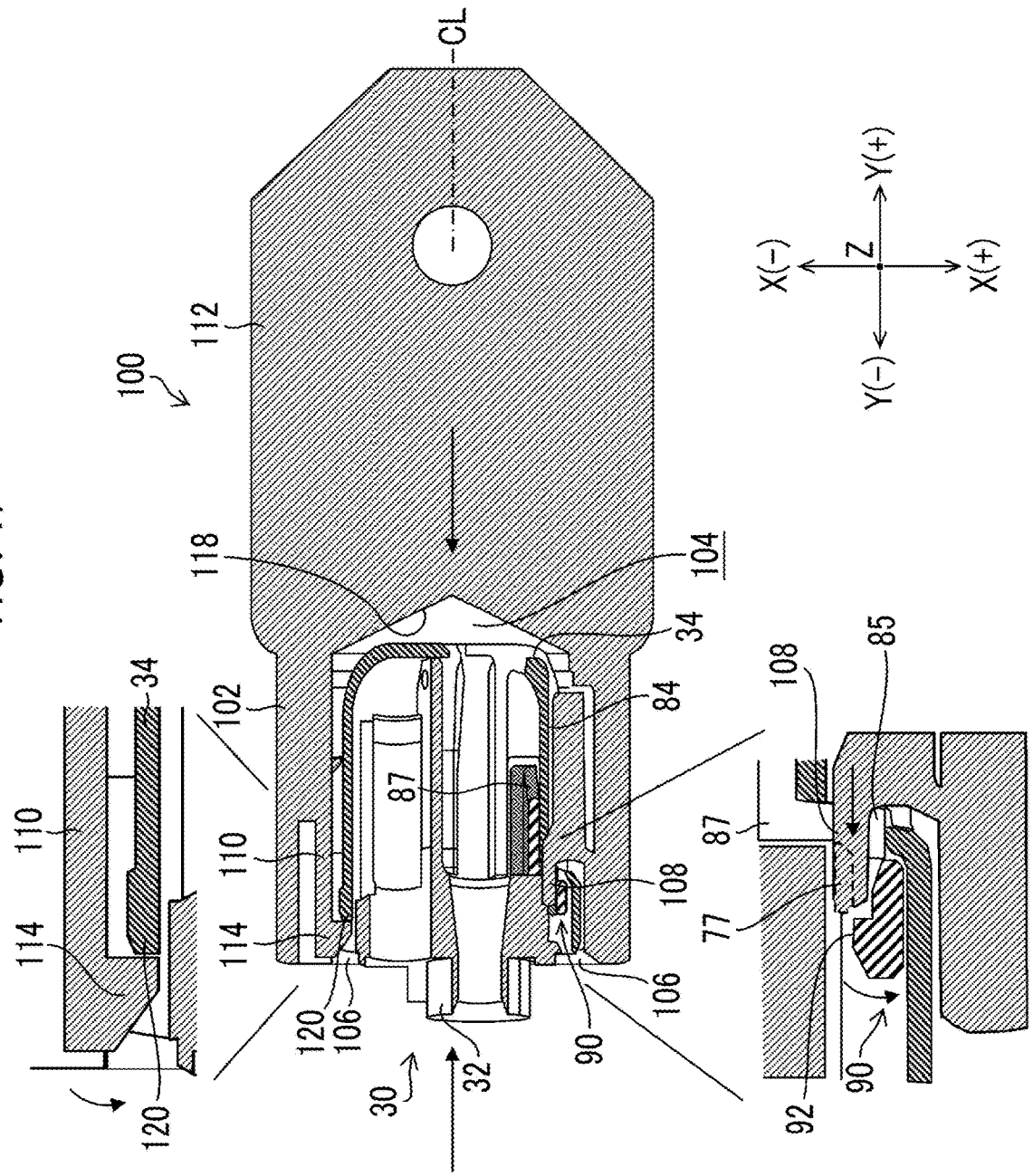
FIG. 17 is a cross-sectional view illustrating the procedure for detaching the distal end cap according to the first embodiment of the distal end cap detachment jig.

FIG. 17 shows a state in which the locking release portion 108 releases the locking between the distal end cap 34 and the distal end portion body 32 and the holding portion 110 holds the end portion of the distal end cap 34 in a state in which the distal end cap 34 of the distal end portion 30 is accommodated in the accommodation space portion 104 of the jig body 102.

As shown in the lower part of FIG. 17, the locking release portion 108 passes through the third opening portion 85 of the distal end cap 34 and the groove portion 78 of the proximal end wall portion 65, and comes into contact with the coupling member 93 through which the claw portions 92 are coupled. Since the locking release portion 108 is thick on the Y(+) direction side, the coupling member 93 is moved to the X(+) direction side as the locking release portion 108 is moved to the Y(−) direction side. As a result, the support members 91 (not shown) are elastically deformed to the X(+) direction side, the claw portions 92 of the locking portion 90 that are locked to the stopper portions 77 are moved in the X(+) direction, and the locking between the locking portion 90 and the stopper portions 77 is released. That is, the locking between the distal end cap 34 and the distal end portion body 32 is released.

As shown in the upper part of FIG. 17, the holding portion 110 goes over the protruding portion 120, the elastic deformation of the holding portion 110 returns to the original state (X(+) direction), and the claw portion 114 is engaged with the end portion of the distal end cap 34 by the snap-fit. The holding portion 110 of the embodiment has a configuration in which the holding portion 110 is caught on the distal end cap. The claw portion 114 goes over the protruding portion 120 and is engaged by the snap-fit when the claw portion 114 is engaged, so that the operator can feel a click feeling and recognize that the distal end portion 30 is inserted into a predetermined position of the distal end cap detachment jig 100. The click feeling allows the operator to avoid pushing the distal end portion 30 more than necessary.

Here, it is preferable that a positional relationship between the locking release portion 108 and the holding portion 110 is a positional relationship (1) in which the release of the locking between the distal end cap 34 and the distal end portion body 32 by the locking release portion 108 and the holding of the distal end cap 34 by the holding portion 110 are performed at the same time, or (2) in which the release of the locking between the distal end cap 34 and the distal end portion body 32 by the locking release portion 108 is performed first and the holding of the distal end cap 34 by the holding portion 110 is performed later. The locking release portion 108 and the holding portion 110 have the above-described positional relationship, so that the distal end cap 34 can be reliably detached from the distal end portion body 32.

Figure 18:
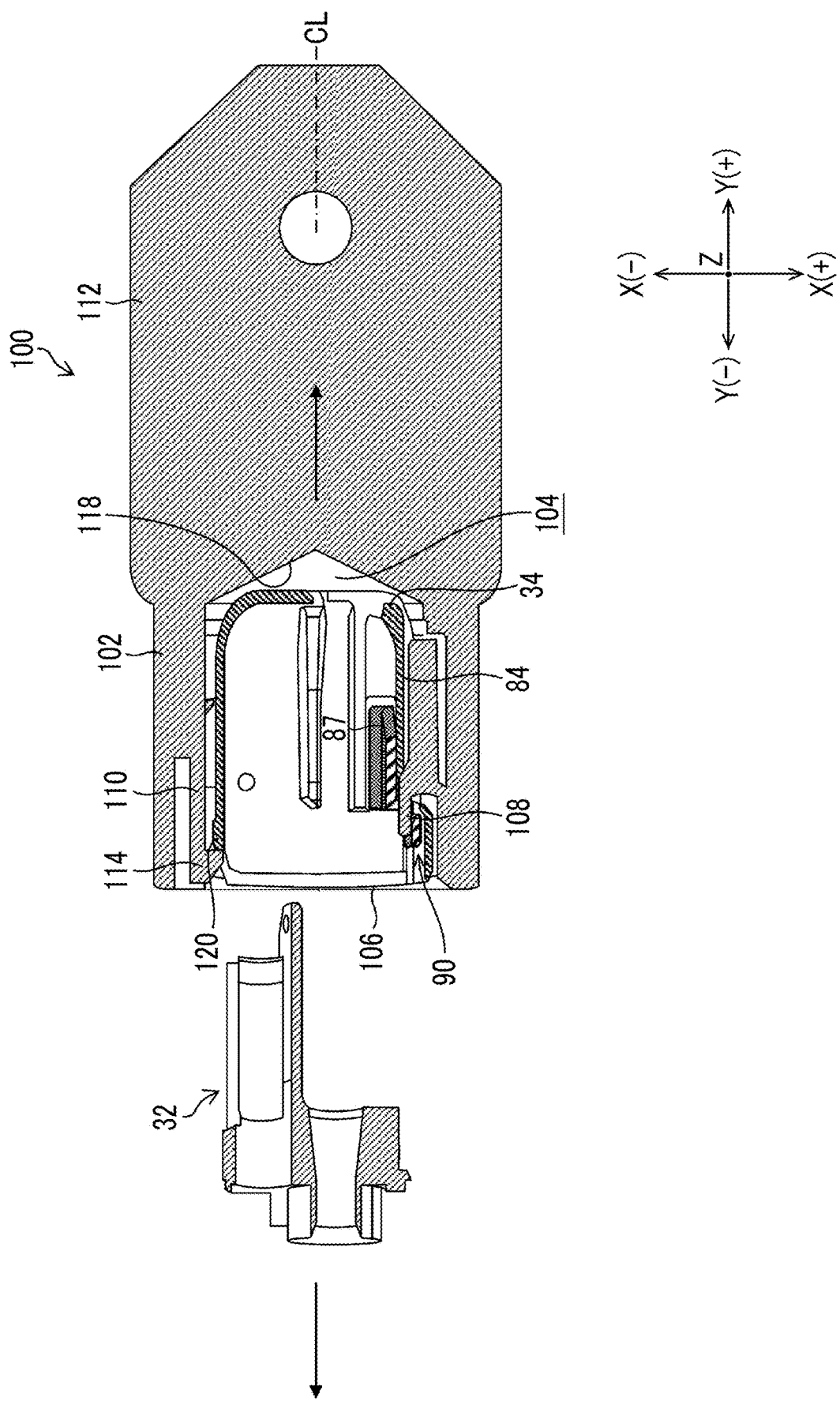
FIG. 18 is a cross-sectional view illustrating the procedure for detaching the distal end cap according to the first embodiment of the distal end cap detachment jig.

FIG. 18 is a view showing a state in which the distal end cap 34 is integrated with the jig body 102 and is pulled out from the distal end portion body 32. In FIG. 17, the locking release portion 108 is in the locking release state in which the locking of the locking portion 90 with respect to the distal end portion body 32 is released, and the holding portion 110 is in the holding state in which the distal end cap is held by the holding portion. In this state, in a case where the distal end cap detachment jig 100 and the distal end portion body 32 are moved relative to each other in a direction away from each other in the Y direction, the distal end cap 34 can be detached from the distal end portion body 32 in a state in which the distal end cap 34 is accommodated in the accommodation space portion 104 of the jig body 102. The distal end cap 34 can be detached without a load applied to the distal end portion body 32. The distal end cap 34 can be easily detached even in a case where the distal end cap 34 is dirty with body fluid.

As shown in FIG. 18, the distal end cap 34 is accommodated in the accommodation space portion 104, and the distal end cap 34 is held by the holding portion 110 on the side of the opening portion 106. In a case where the jig body 102 has the bottom portion 118, it is necessary to take out the distal end cap 34 through the opening portion 106 in order to take out the distal end cap 34 from the accommodation space portion 104. However, it is difficult to take out the distal end cap 34 from the accommodation space portion 104 because the holding portion 110 restricts the distal end cap 34 from being moved to the opening portion 106. In a case where the distal end cap 34 and the jig body 102 are made disposable, it is possible to prevent the distal end cap 34 from being reused by making it difficult to take out the distal end cap 34, which is preferable. The distal end cap detachment jig 100 is discarded with the distal end cap 34 accommodated. In a case where the jig body 102 has the bottom portion 118, the jig body 102 is suitable for use as a disposable.

Figure 19:
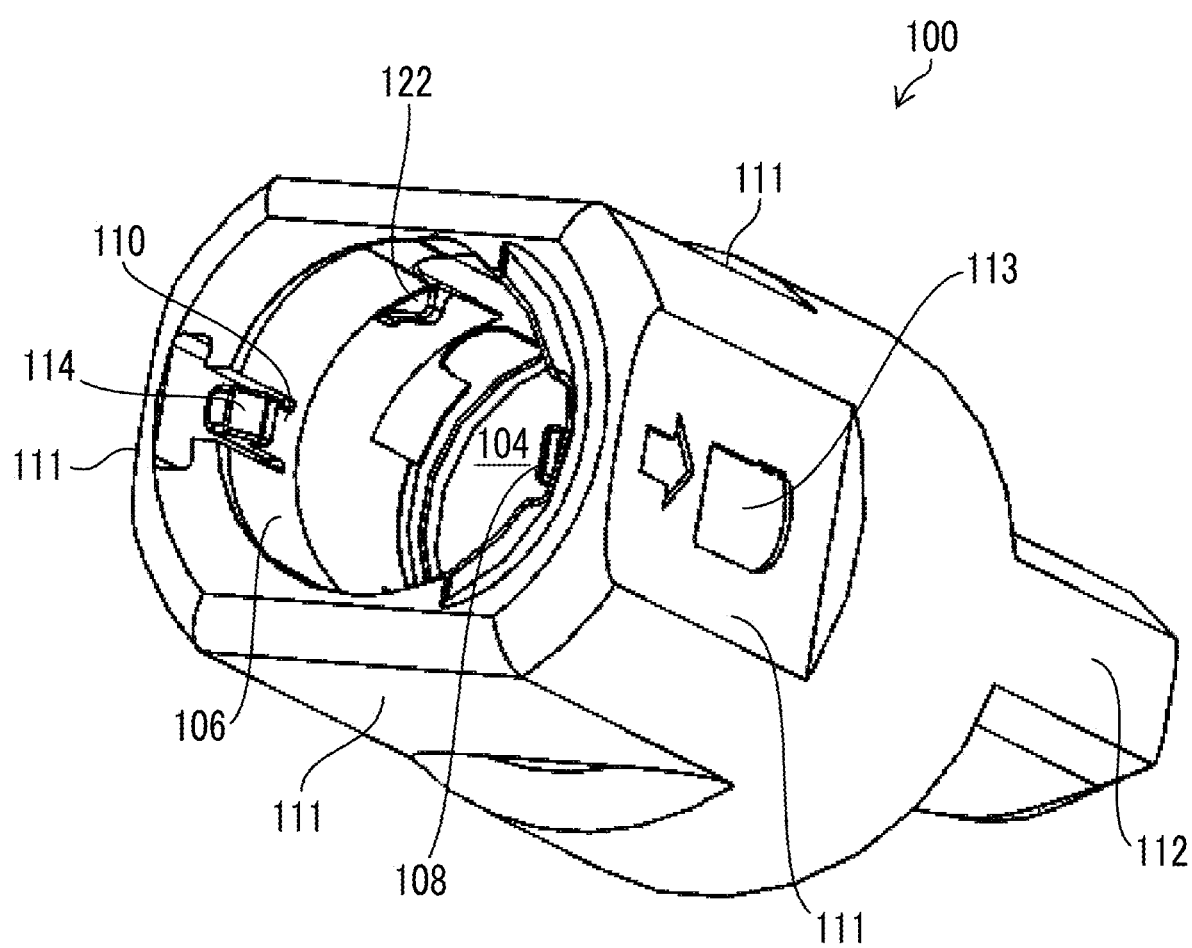
FIG. 19 is a view illustrating a restriction portion provided in the distal end cap detachment jig.

Next, a preferable aspect of the distal end cap detachment jig 100 will be described. FIG. 19 is a perspective view of the distal end cap detachment jig 100 as viewed from the side of the opening portion 106. As shown in FIG. 19, a restriction portion 122 is provided in the accommodation space portion 104 of the jig body 102. The restriction portion 122 restricts the distal end cap 34 (distal end portion 30) from being inserted into the distal end cap detachment jig 100 from the circumferentially wrong direction. The restriction portion 122 allows the operator to recognize the circumferentially wrong insertion direction.

Figure 20A:
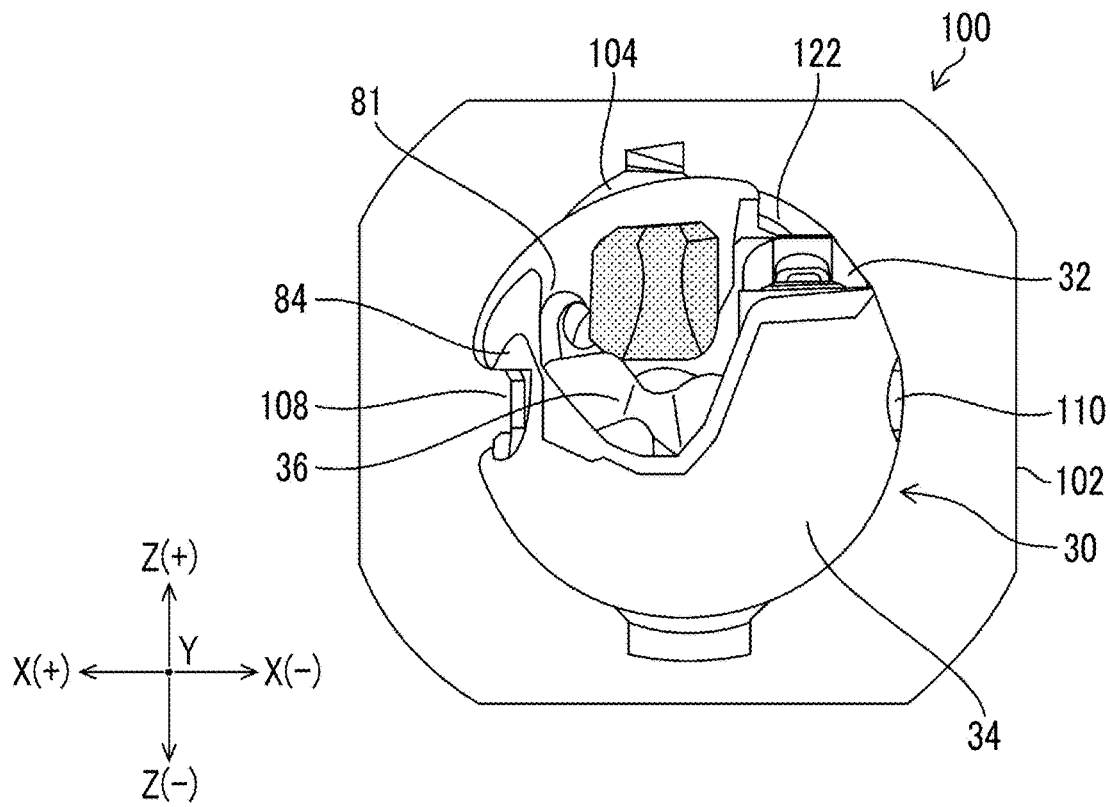
FIGS. 20A and 20B are views illustrating a relationship between an insertion direction of the distal end cap detachment jig and the restriction portion.
Figure 20B:
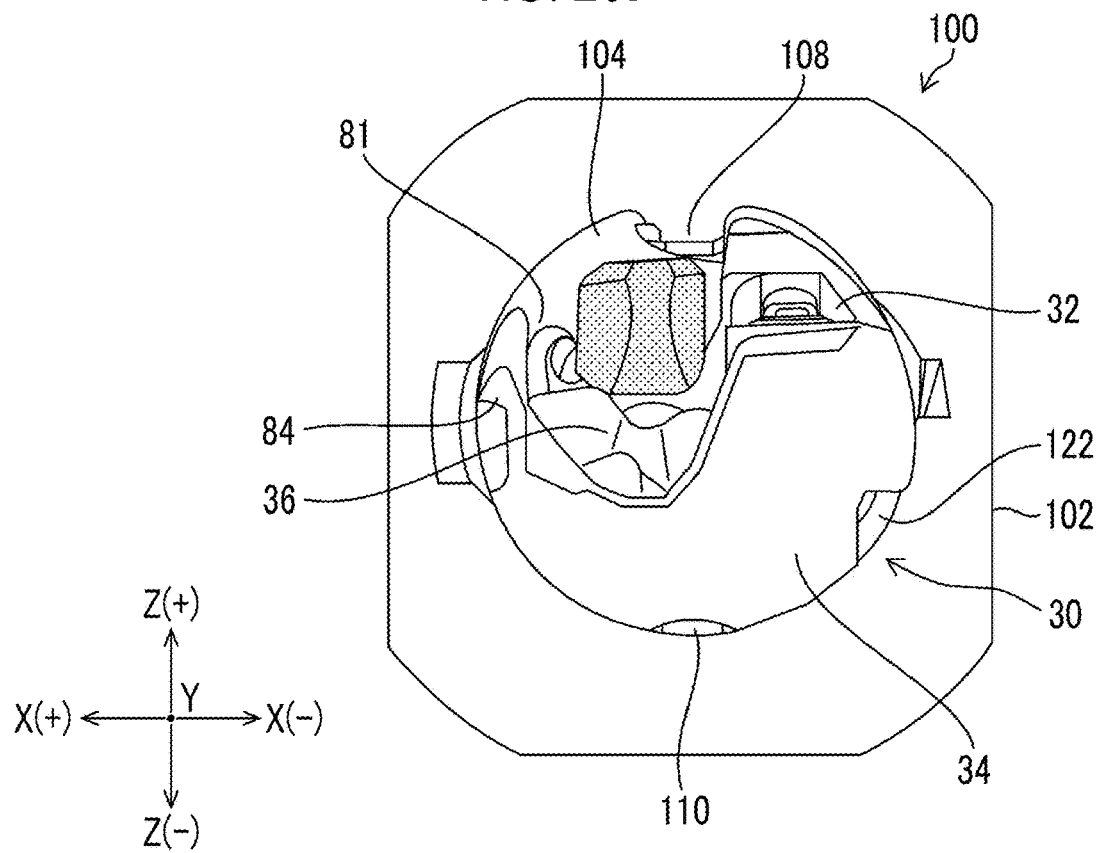

FIGS. 20A and 20B are views illustrating a case where the distal end portion 30 is inserted into the distal end cap detachment jig 100 at a correct insertion angle (FIG. 20A) and a case where the distal end portion 30 is mounted on the distal end cap detachment jig 100 at a wrong insertion angle (FIG. 20B). FIGS. 20A and 20B are views of the distal end portion 30 and the distal end cap detachment jig 100 when viewed from the Y(+) direction side.

As shown in FIG. 20A, in a case where the distal end portion 30 is inserted at the correct insertion angle, the locking release portion 108 is inserted into the groove portion 84 as described above, and the distal end portion 30 is accommodated in the distal end cap detachment jig 100 while being guided. Since the restriction portion 122 does not come into contact with either the distal end portion body 32 or the distal end cap 34 of the distal end portion 30, the distal end portion 30 can move to a predetermined position of the accommodation space portion 104.

On the other hand, the distal end portion 30 can be inserted into the distal end cap detachment jig 100 because the locking release portion 108 can pass through the side of the first opening portion 81 of the distal end cap 34 even in a case where the insertion direction of the distal end cap 34 into the distal end cap detachment jig 100 is incorrect, as shown in FIG. 20B. Then, the operator may recognize that the locking release portion 108 is inserted into the groove portion 84 and the distal end cap 34 is inserted into the jig body 102 in the correct insertion direction by the guide function. There is a concern that a load may be applied to the distal end portion 30 and the like in a case where the distal end cap 34 is inserted into the jig body 102 in that state. In that regard, the restriction portion 122 is provided in the jig body 102, whereby the restriction portion 122 comes into contact with the distal end cap 34 to restrict the distal end cap 34 from being moved to the inside of the distal end cap detachment jig 100.

As shown in FIG. 21, in a case where the insertion direction of the distal end cap 34 into the jig body 102 is circumferentially incorrect, the distal end portion 30 is not inserted into a predetermined position of the distal end cap detachment jig 100 due to the restriction portion 122 (not shown). Since the distal end portion 30 is not moved to the side of the distal end cap detachment jig 100, the operator can notice that the insertion direction is wrong on the way.

Second Embodiment

Next, a second embodiment of the distal end cap detachment jig will be described. The same configurations as those of the first embodiment are designated by the same reference numerals, and the detailed description thereof may be omitted.

FIGS. 22A and 22B are cross-sectional views of the second embodiment of the distal end cap detachment jig and show a state after the distal end cap 34 is detached from the distal end portion body 32.

As shown in FIGS. 22A and 22B, a distal end cap detachment jig 200 of the second embodiment does not comprise the bottom portion 118 unlike the distal end cap detachment jig 100 of the first embodiment. The distal end cap detachment jig 200 has an open portion 124 that is open to the accommodation space portion 104 on the side of the other end opposite to the opening portion 106 provided at the one end. The open portion 124 is formed in a size that allows the distal end cap 34 to be discharged to the outside from the accommodation space portion 104.

As shown in FIG. 22A, the distal end cap 34 is detached from the distal end portion body 32 by the distal end cap detachment jig 200 and is held in the accommodation space portion 104.

As shown in FIG. 22B, the open portion 124 is formed in a size that allows the distal end cap 34 to be discharged to the outside from the accommodation space portion 104. Accordingly, it is possible to easily take out the distal end cap 34 from the open portion 124 by applying a force from the side of the opening portion 106. Since the distal end cap 34 is taken out, the distal end cap detachment jig 200 can be reused.

Third Embodiment

Next, a third embodiment of the distal end cap detachment jig will be described. The same configurations as those of the first and second embodiments are designated by the same reference numerals, and the detailed description thereof may be omitted. FIG. 23 is a cross-sectional view of the third embodiment of the distal end cap detachment jig and shows a state immediately before the distal end cap 34 is inserted into the jig body 102.

As shown in FIG. 23, the distal end cap 34 has a notch portion 126 formed on the outer peripheral surface on the X(−) direction side. As shown in the enlarged view, the notch portion 126 has a rectangular shape in a cross-sectional view.

A distal end cap detachment jig 300 comprises a holding portion 128 protruding toward the side of the accommodation space portion 104 of the jig body 102. As shown in the enlarged view, the holding portion 128 has an inclined surface on the side of the opening portion 106 and a plane on the side opposite to the opening portion 106. The inclined surface approaches the central axis CL as the inclined surface is farther away from the opening portion 106. Meanwhile, the plane is substantially orthogonal to the central axis CL.

In a case where the distal end cap detachment jig 300 is moved to a predetermined position with respect to the distal end portion 30, the locking between the locking portion 90 and the stopper portions 77 (not shown) are released by the locking release portion 108, and the holding portion 128 is inserted into the notch portion 126 to hold the distal end cap 34 at the same time as the release of the locking or after the release of the locking.

When the distal end cap 34 is detached from the distal end portion body 32, the plane of the holding portion 128 of the jig body 102 is caught on the notch portion 126 of the distal end cap 34, and the distal end cap 34 is integrated with the jig body 102 and is detached from the distal end portion body 32.

In the third embodiment, the holding portion 128 is provided at a position farther from the opening portion 106 of the accommodation space portion 104 as compared with the holding portion 110 of the first embodiment. Since the distal end cap 34 is held by the holding portion 128 at a position farther from the opening portion 106, the distal end cap 34 has a structure that makes it difficult to take out the distal end cap 34 from the distal end cap detachment jig 300 as compared with that of the first embodiment so that the distal end cap 34 can be effectively prevented from being reused.

Fourth Embodiment

Next, a fourth embodiment of the distal end cap detachment jig will be described. The same configurations as those of the first to third embodiments are designated by the same reference numerals, and the detailed description thereof may be omitted. FIGS. 24A and 24B are cross-sectional views of the fourth embodiment of the distal end cap detachment jig and show a state immediately before the distal end cap 34 is inserted into the jig body 102 and a state in which the distal end cap 34 is inserted into the jig body 102.

As shown in FIG. 24A, a distal end cap detachment jig 400 comprises two holding portions 130 each protruding toward the side of the accommodation space portion 104 of the jig body 102. The two holding portions 130 are provided at positions facing each other with the accommodation space portion 104 interposed therebetween, and each holding portion 130 has a semi-elliptical shape protruding toward the central axis CL.

As shown in FIG. 24B, in a case where the distal end cap detachment jig 400 is moved to a predetermined position with respect to the distal end portion 30, the locking between the locking portion 90 and the stopper portions 77 (not shown) are released by the locking release portion 108, and the holding portions 130 grip and hold the distal end cap 34 from both sides at the same time as the release of the locking or after the release of the locking.

When the distal end cap 34 is detached from the distal end portion body 32, the holding portions 130 of the jig body 102 grip the distal end cap 34 and the distal end cap 34 is held in the accommodation space portion 104, whereby the distal end cap 34 is integrated with the jig body 102 and is detached from the distal end portion body 32. The distal end cap detachment jig 400 does not need to have unevenness for catching on the outer peripheral surface of the distal end cap 34 as in the holding portions 110 and 128.

Other Embodiments

In the endoscope 10 shown in FIG. 1, a mounting component (not shown) can be attachably and detachably provided on the operation part 22. As the mounting component, for example, a coupling mechanism that is used to couple the other end of the wire 38 having one end attached to the elevator 36 to a driving mechanism of the elevating operation lever 20 is conceivable.

A configuration is employed in which the distal end cap detachment jigs of the first to fourth embodiments are each included in the mounting component, so that it is possible to prevent the distal end cap detachment jig from being lost. Further, the mounting component corresponds to the configuration of the endoscope 10 to be used and the distal end cap detachment jig of the mounting component corresponds to the distal end cap 34 used for the endoscope 10, so that it is possible to prevent misuse of the distal end cap detachment jig.

Although the present invention has been described heretofore, it goes without saying that the present invention is not limited to the above-described examples and various improvements or modifications may be made without departing from the gist of the present invention.

EXPLANATION OF REFERENCES

10: endoscope
12: endoscope system
14: endoscope processor apparatus
15: light source device
15A: processor-side connector
16: image processing device
18: display 20: elevating operation lever
22: operation part
24: endoscope insertion part
26: soft portion
28: bendable portion
30: distal end portion
32: distal end portion body
34: distal end cap
36: treatment tool elevator (elevator)
36a: treatment tool guide surface
37: treatment tool channel
38: elevating operation wire (wire)
40: wire channel
42: air/water supply tube
44: cable insertion channel
46: operation part body
48: grip portion
50: bending-proof pipe
52: universal cable
54: connector device
57: air/water supply button
58: air/water supply nozzle
59: suction button
60: treatment tool outlet port
61: wire insertion hole
62: angle knob
64: treatment tool inlet port
65: proximal end wall portion
66: elevator accommodation space
68: partition wall
74: illumination window
76: observation window
77: stopper portion
78: groove portion
80: body portion
81: first opening portion
82: distal end surface portion
83: second opening portion
84: groove portion
85: third opening portion
86: bearing
87: wall member
88: rotary shaft
90: locking portion
91: support member
92: claw portion
93: coupling member
100: distal end cap detachment jig
102: jig body
104: accommodation space portion
106: opening portion
108: locking release portion
110: holding portion
111: plane
112: plate-shaped member
113: indicator
114: claw portion
118: bottom portion
120: protruding portion
122: restriction portion
124: open portion
126: notch portion
128: holding portion
130: holding portion
200: distal end cap detachment jig
300: distal end cap detachment jig
400: distal end cap detachment jig Ax: major axis direction
CL: central axis

What is claimed is:

1. A distal end cap detachment jig configured to detach a distal end cap from a distal end portion body of an endoscope insertion part, wherein the distal end cap is attachable to and detachable from the distal end portion body and has a locking portion capable of being locked to the distal end portion body when the distal end cap is mounted on the distal end portion body, and the locking portion comprises a claw, the distal end cap detachment jig comprising:
a jig body having an accommodation space portion of which one end is provided with an opening portion;
a locking release portion provided in the jig body, wherein the locking release portion comprises a protrusion; and
a holding portion provided in the jig body, wherein the holding portion comprises a protrusion,
wherein the locking release portion is configured such that when the distal end cap is accommodated in the accommodation space portion, the locking release portion causes the locking portion to release the distal end cap from the distal end portion body, and
the holding portion is configured such that when the distal end cap is accommodated in the accommodation space portion, the holding portion holds the distal end cap in the jig body so that the distal end cap is capable of being pulled out from the distal end portion body.

2. The distal end cap detachment jig according to claim 1, wherein the jig body has a bottom portion that closes the accommodation space portion and that is provided on a side of the other end opposite to the one end.

3. The distal end cap detachment jig according to claim 1, wherein the jig body has an open portion that is open to the accommodation space portion and that is provided on a side of the other end opposite to the one end.

4. The distal end cap detachment jig according to claim 3, wherein the open portion is configured to be formed in a size that allows the distal end cap pulled out from the distal end portion body to be discharged to an outside from the accommodation space portion.

5. The distal end cap detachment jig according to claim 1, wherein the distal end cap has a guide portion,
the locking release portion is configured to engage with the guide portion, and
the locking release portion is configured such that when the distal end cap is accommodated in the accommodation space portion, the locking release portion is engaged with the guide portion and is guided so that the locking release portion and the locking portion are aligned with each other.

6. The distal end cap detachment jig according to claim 1, wherein the jig body has a restriction portion configured to restrict the distal end cap from being inserted from a circumferentially wrong direction, and the restriction portion comprises a protrusion.

7. The distal end cap detachment jig according to claim 1, wherein the holding portion is configured to be caught on the distal end cap.

8. The distal end cap detachment jig according to claim 7, wherein the holding portion is configured to engage with the distal end cap by a snap-fit.

9. The distal end cap detachment jig according to claim 1, wherein the holding portion is configured to grip the distal end cap.

10. The distal end cap detachment jig according to claim 1,
wherein the jig body has an indicator configured to indicate an accommodation direction of the distal end cap with respect to the accommodation space portion.

11. The distal end cap detachment jig according to claim 1,
wherein the jig body is a disposable.

12. The distal end cap detachment jig according to claim 1,
wherein the distal end cap detachment jig is configured such that a positional relationship between the locking release portion and the holding portion is a positional relationship
in which the release of the locking between the distal end cap and the distal end portion body by the locking release portion and the holding of the distal end cap by the holding portion are performed at the same time, or
in which the release of the locking between the distal end cap and the distal end portion body by the locking release portion is performed first and the holding of the distal end cap by the holding portion is performed later.

13. An endoscope comprising:
an operation part provided with an operation member;
an endoscope insertion part provided on a distal end side of the operation part and configured to be inserted into an object to be examined;
a distal end portion body provided on a distal end side of the endoscope insertion part;
a distal end cap configured to be attachable to and detachable from the distal end portion body and being provided with a locking portion capable of being locked to the distal end portion body when the distal end cap is mounted on the distal end portion body, wherein the locking portion comprises a claw; and
a mounting component configured to be attachably and detachably mounted on the operation part,
wherein the mounting component includes the distal end cap detachment jig according to claim 1.

* * * * *